US011287423B2

(12) United States Patent
Gorelik et al.

(10) Patent No.: US 11,287,423 B2
(45) Date of Patent: *Mar. 29, 2022

(54) ASSAY FOR JC VIRUS ANTIBODIES

(71) Applicant: Biogen MA Inc., Cambridge, MA (US)

(72) Inventors: Leonid Gorelik, Quincy, MA (US); Kenneth J. Simon, Cambridge, MA (US); Meena Subramanyam, Stoneham, MA (US); Mia Marie Rushe, Everett, MA (US)

(73) Assignee: Biogen MA Inc., Cambridge, MA (US)

( * ) Notice: Subject to any disclaimer, the term of this patent is extended or adjusted under 35 U.S.C. 154(b) by 144 days.

This patent is subject to a terminal disclaimer.

(21) Appl. No.: 16/594,843

(22) Filed: Oct. 7, 2019

(65) Prior Publication Data

US 2021/0102939 A1   Apr. 8, 2021

Related U.S. Application Data

(60) Continuation of application No. 15/063,777, filed on Mar. 8, 2016, now Pat. No. 10,444,234, which is a division of application No. 13/521,311, filed as application No. PCT/US2011/020832 on Jan. 11, 2011, now Pat. No. 9,316,641.

(60) Provisional application No. 61/316,193, filed on Mar. 22, 2010, provisional application No. 61/294,048, filed on Jan. 11, 2010.

(51) Int. Cl.
  *G01N 33/543*    (2006.01)
(52) U.S. Cl.
  CPC .............. *G01N 33/54306* (2013.01)

(58) Field of Classification Search
  None
  See application file for complete search history.

(56) References Cited

U.S. PATENT DOCUMENTS

| 3,817,837 A | 6/1974 | Rubenstein et al. |
| 3,850,752 A | 11/1974 | Schuurs et al. |

(Continued)

FOREIGN PATENT DOCUMENTS

| EP | 1712913 A1 | 10/2006 |
| EP | 1933140 A1 | 6/2008 |

(Continued)

OTHER PUBLICATIONS

U.S. Appl. No. 16/211,154, entitled, "Method of Assessing Risk of PML", filed Dec. 5, 2018, of Biogen MA Inc. (Published as 2019-0227064 on Jul. 25, 2019).

(Continued)

*Primary Examiner* — Michelle S Horning
(74) *Attorney, Agent, or Firm* — Todd Lorenz

(57) ABSTRACT

The disclosure relates to methods and reagents for analyzing samples for the presence of JC virus antibodies. Disclosed is a method that includes obtaining a biological sample from a subject (e.g., plasma, serum, blood, urine, or cerebrospinal fluid), contacting the sample with highly purified viral-like particles (HPVLPs) under conditions suitable for binding of a JCV antibody in the sample to an HPVLP, and detecting the level of JCV antibody binding in the sample to HPVLP. In one embodiment, determining the level of anti-JCV antibodies in the subject sample provides a method of identifying PML risk in a subject.

26 Claims, 6 Drawing Sheets

(56) References Cited

U.S. PATENT DOCUMENTS

| | | | |
|---|---|---|---|
| 3,939,350 | A | 2/1976 | Kronick et al. |
| 3,996,345 | A | 12/1976 | Ullman et al. |
| 4,235,601 | A | 11/1980 | Deutsch et al. |
| 4,275,149 | A | 6/1981 | Deutsch et al. |
| 4,277,437 | A | 7/1981 | Maggio |
| 4,366,241 | A | 12/1982 | Tom et al. |
| 4,376,110 | A | 3/1983 | David et al. |
| 4,391,904 | A | 7/1983 | Litman et al. |
| 4,517,288 | A | 5/1985 | Giegel et al. |
| 4,703,017 | A | 10/1987 | Campbell et al. |
| 4,818,677 | A | 4/1989 | Hay-Kaufman et al. |
| 4,837,168 | A | 6/1989 | de Jaeger et al. |
| 4,943,522 | A | 7/1990 | Eisinger et al. |
| 5,096,837 | A | 3/1992 | Fan et al. |
| 5,118,428 | A | 6/1992 | Sand et al. |
| 5,118,630 | A | 6/1992 | Glaze |
| 5,221,616 | A | 6/1993 | Kolb et al. |
| 5,223,220 | A | 6/1993 | Fan et al. |
| 5,225,328 | A | 7/1993 | Chang |
| 5,329,459 | A | 7/1994 | Kaufman et al. |
| 5,415,994 | A | 5/1995 | Imrich et al. |
| 5,434,057 | A | 7/1995 | Dorian |
| 5,521,102 | A | 5/1996 | Boehringer et al. |
| 5,536,646 | A | 7/1996 | Sand et al. |
| 5,541,069 | A | 7/1996 | Mortensen et al. |
| 5,559,041 | A | 9/1996 | Kang et al. |
| 5,686,315 | A | 11/1997 | Pronovost et al. |
| 5,712,172 | A | 1/1998 | Huang et al. |
| 5,763,262 | A | 6/1998 | Wong et al. |
| 5,766,961 | A | 6/1998 | Pawlak et al. |
| 5,770,460 | A | 6/1998 | Pawlak et al. |
| 5,773,234 | A | 6/1998 | Pronovost et al. |
| 5,786,220 | A | 7/1998 | Pronovost et al. |
| 5,804,452 | A | 9/1998 | Pronovost et al. |
| 5,814,455 | A | 9/1998 | Pronovost et al. |
| 5,840,299 | A | 11/1998 | Bendig et al. |
| 5,845,255 | A | 12/1998 | Mayaud |
| 5,939,331 | A | 8/1999 | Burd et al. |
| 6,014,631 | A | 1/2000 | Teagarden et al. |
| 6,033,665 | A | 3/2000 | Yednock |
| 6,187,598 | B1 | 2/2001 | May et al. |
| 6,229,011 | B1 | 5/2001 | Chen et al. |
| 6,238,859 | B1 | 5/2001 | Luke et al. |
| 6,305,377 | B1 | 10/2001 | Portwood et al. |
| 6,306,642 | B1 | 10/2001 | Nelson et al. |
| 6,352,862 | B1 | 3/2002 | Davis et al. |
| 6,388,084 | B1 | 5/2002 | Kaplan et al. |
| 6,485,982 | B1 | 11/2002 | Charlton |
| 6,534,320 | B2 | 3/2003 | Ching et al. |
| 6,551,593 | B1 | 4/2003 | Ringler et al. |
| 6,602,503 | B1 | 8/2003 | Lobb et al. |
| 6,605,602 | B1 | 8/2003 | Vats |
| 6,620,626 | B1 | 9/2003 | Bodily |
| 6,623,981 | B2 | 9/2003 | Billheimer et al. |
| 6,767,714 | B2 | 7/2004 | Nazareth et al. |
| 6,790,611 | B2 | 9/2004 | Lassen et al. |
| 7,008,949 | B2 | 3/2006 | Konradi et al. |
| 7,026,328 | B2 | 4/2006 | Konradi et al. |
| 7,026,501 | B2 | 4/2006 | Kawaguchi et al. |
| 7,101,855 | B2 | 9/2006 | Dressen et al. |
| 7,129,053 | B1 | 10/2006 | Reiter et al. |
| 7,419,666 | B1 | 9/2008 | Iliaki et al. |
| 7,718,444 | B2 | 5/2010 | Takizawa et al. |
| 7,807,167 | B2 | 10/2010 | Taylor et al. |
| 8,410,115 | B2 | 4/2013 | Lieberburg |
| 9,316,641 | B2 * | 4/2016 | Gorelik ............ G01N 33/56983 |
| 9,493,567 | B2 | 11/2016 | Lieberburg |
| 10,119,976 | B2 | 11/2018 | Bloomgren et al. |
| 10,233,245 | B2 | 3/2019 | Lieberburg |
| 10,444,234 | B2 * | 10/2019 | Gorelik ............ G01N 33/56983 |
| 10,677,803 | B2 | 6/2020 | Bloomgren et al. |
| 2001/0021910 | A1 | 9/2001 | Goldstein |
| 2002/0052543 | A1 | 5/2002 | Williams et al. |
| 2002/0197233 | A1 | 12/2002 | Relton et al. |
| 2003/0032923 | A1 | 2/2003 | Eakins et al. |
| 2003/0176498 | A1 | 9/2003 | Kawaguchi et al. |
| 2003/0186327 | A1 | 10/2003 | Babcook |
| 2004/0009169 | A1 | 1/2004 | Taylor et al. |
| 2004/0138243 | A1 | 7/2004 | Konradi et al. |
| 2004/0142954 | A1 | 7/2004 | Konradi et al. |
| 2004/0248216 | A1 | 12/2004 | Seino |
| 2005/0215869 | A1 | 9/2005 | Elsayed et al. |
| 2005/0283385 | A1 | 12/2005 | Hunkeler et al. |
| 2006/0009385 | A1 | 1/2006 | Hoffman et al. |
| 2006/0013799 | A1 | 1/2006 | Konradi et al. |
| 2007/0142416 | A1 | 6/2007 | Semko et al. |
| 2007/0190667 | A1 | 8/2007 | Cole et al. |
| 2007/0207141 | A1 | 9/2007 | Lieburgurg |
| 2007/0231319 | A1 | 10/2007 | Yednock |
| 2007/0275481 | A1 | 11/2007 | Vasilyeva et al. |
| 2008/0044382 | A1 | 2/2008 | Lieberburg |
| 2008/0058357 | A1 | 3/2008 | Smith et al. |
| 2008/0233150 | A1 | 9/2008 | Smith et al. |
| 2009/0010926 | A1 | 1/2009 | Panzara et al. |
| 2009/0169477 | A1 | 7/2009 | Panzara et al. |
| 2009/0176256 | A1 | 7/2009 | Subramanyam et al. |
| 2009/0216107 | A1 | 8/2009 | Rubin et al. |
| 2012/0177642 | A1 | 7/2012 | Yednock |

FOREIGN PATENT DOCUMENTS

| | | |
|---|---|---|
| EP | 1485127 B1 | 6/2011 |
| EP | 2645106 A2 | 10/2013 |
| EP | 2676967 B1 | 8/2019 |
| WO | WO 1992/19774 A1 | 11/1992 |
| WO | WO 1994/16094 A2 | 7/1994 |
| WO | WO 1997/19174 A1 | 5/1997 |
| WO | WO 2003/016902 A1 | 2/2003 |
| WO | WO 2003/072040 A2 | 9/2003 |
| WO | WO 2004/001539 A2 | 12/2003 |
| WO | WO 2006/107962 A2 | 10/2006 |
| WO | WO 2006/112951 A2 | 10/2006 |
| WO | WO 2007/041270 A1 | 4/2007 |
| WO | WO 2007/100763 A2 | 9/2007 |
| WO | WO 2007/100770 A2 | 9/2007 |
| WO | WO 2007/101165 A1 | 9/2007 |
| WO | WO 2007/103112 A2 | 9/2007 |
| WO | WO 2010/090757 A1 | 8/2010 |
| WO | WO 2010/096674 A2 | 8/2010 |
| WO | WO 2011/085369 A1 | 7/2011 |
| WO | WO 2012/166971 A2 | 12/2012 |

OTHER PUBLICATIONS

U.S. Appl. No. 17/393,335, entitled, "Method of Assessing Risk of PML", filed Aug. 3, 20221, of Biogen MA Inc.

U.S. Appl. No. 16/357,179, entitled, "Methods of Treating Inflammatory and Autoimmune Diseases With Natalizumab", filed Mar. 18, 2019, of Biogen MA Inc. (Published as 2019-0315871 on Oct. 17, 2019).

U.S. Appl. No. 16/588,098, entitled, "Methods of Treating Inflammatory and Autoimmune Diseases With Natalizumab", filed Sep. 30, 2019, of Biogen MA Inc. (Published as 2020-0166521 on May 28, 2020).

U.S. Appl. No. 16/896,074, entitled, "Method of Assessing Risk of PML", filed Jun. 9, 2020, of Biogen MA Inc. (Published as 2020-0408776 on Dec. 31, 2020).

Aalberse et al., "IgG4 breaking the rules", Immunology, vol. 105, No. 1, pp. 9-19 (2002).

Abbing et al., "Efficient Intracellular Delivery of a Protein and a Low Molecular Weight Substance via Recombinant Particles", The Journal of Biological Chemistry, vol. 279, No. 25, pp. 27410-27421, (2004).

Abraham et al., "A Small-Molecule, Tight-binding Inhibitor of the Integrin a4131 Blocks Antigen-induced Airway Responses and Inflammation in Experimental Asthma in Sheep," Am. J. Respir. Crit. Care Med., 162:603-611 (2000).

Achiron, et al., "Does the Flap of a Butterfly's Wings in Brazil set off a Tornado in Texas? The JC Virus Story in Multiple Sclerosis", IMAJ, pp. 283-285 (2005).

(56) References Cited

OTHER PUBLICATIONS

Agostini et al., "JC Virus (JCV) Genotypes in Brain Tissue from Patients with Progressive Multifocal Leukoencephalopathy (PML) and in Urine from Controls without PML: Increased Frequency of JCV Type 2 in PML", Journal of Infectious Diseases, vol. 176, No. 1, p. 6, (1997).
Agostini et al., "Genotype Profile of Human Polyomavirus JC Excreted in Urine of Immunocompetent Individuals," J. Clin. Microbiol., 34:159-164 (1996).
Ahsan, N, and Shah, KV, "Polyomaviruses and human diseases.—chapter 1", Retinal Degenerative Diseases: Advances in Experimental Medicine and Biology, Springer, US, vol. 577, pp. 1-18, (2006).
Albrecht et al., "Highly active antiretroviral therapy significantly improves the prognosis of patients with HIV-associated progressive multifocal leukoencephalopathy," AIDS, 12:11491154 (1998).
Anonymous, "Natalizumab in the Treatment of Rheumatoid Arthritis in Subjects Receiving Methotrexate", US National Library of Medicine ClinicalTrials.gov, (2009), pp. 1-10, downloaded from https://clinicaltrials.gov/ct2/show/results/NCT00083759?view=results.
Attwood, et al., "The Babel of Bioinformatics," Science, vol. 290, No. 5491, pp. 471-473 (2000).
Baker et al., "Protein Structure Predication and Structural Genomics," Science, vol. 294, No. 5540, pp. 93-96 (2001).
Baron et al., "Surface Expression of a4 Integrin by CD4 T Cells Is Required for Their Entry Into Brain Parenchyma," J. Exp. Med., 177:57-68 (1993).
Behzhad-Behbahani et al., Detection of BK virus and JC virus DNA in urine samples from immunocompromised (HIV-infected) and Immunocometent (HIV-non-Infected) patients using polymerase chain reaction and microplate hybridisation J Clin Virol. Apr. 29, 2004(4), pp. 224-229.
Benedict et al., "Personality Disorder in Myltiple Sclerosis Correlates With Cognititve Impairment", J Neuropsychiatry Clin Neurosci, vol. 13, pp. 70-76 (2001).
Berger et al., "Predictive Factors for Prolonged Survival in Acquired Immunodeficiency Syndrome-Associated Progressive Multifocal Leukoencephalopathy," Ann. Neurol., 44:341349 (1998).
Berger, J.R. and Major, E.O., "Progressive Multifocal Leukoencephalopathy", Seminars in Neurology, vol. 19, No. 2, pp. 193-200 (1999).
Berger, Jr, Nath, A, Progressive multifocal leukoencephalopathy, Cecil's Textbook of Internal Medicine, 21st Ed., W.B. Saunders, Philadephia, PA, Chapeter 479.4, pp. 2137-2138 (2000).
Berger, Jr et al.: "Progressive multifocal leukoencephalopathy and natalizumab—Unforseen consequences"; New Egland Journal of Medicine, vol. 353, No. 4, pp. 414-416 (2005).
Berger, Jr et al.: "Progressive multifocal leukoencephalopathy: lessons from AIDS and natalizumab", Neurological Research, vol. 28, pp. 299-305 (2006).
Biogen Press Release, Nov. 23, 2004, FDA grants accelerated approval of YSABRI, formerly antegren for the treatment of MS. "Biogen Idec and Elan Announce Voluntary Suspension of Tysabri®", Feb. 28, 2005 (Feb. 28, 2005), (//www.biogenidec.com/press_archive. aspx?ID=6015).
Bitsch et al., "Acute axonal injury in multiple sclerosis Correlation with Demyelination and inflammation," Brain, vol. 123, pp. 1174-1183 (2000).
Bjartmar et al., "Axonal pathology in myelin disorders," J. Neurocytol., vol. 28, pp. 383-395 (1999).
Bjartmar, C. and Trapp, B.D., "Axonal and neuronal degeneration in multiple sclerosis: mechanisms and functional consequences," Curr. Opin. Neurol., vol. 14, pp. 171-278 (2001).
Bloomgren, G. et al. "Risk of Natalizumab-Associated Progressive Multifocal Leukoencephalopathy", N Engl J Med., vol. 366, pp. 1870-1880 (2012).
Bozic et al., "Anti-John Cunningham virus antibody prevalence in multiple sclerosis patients: baseline results of STRATIFY-1." Ann Neurol., 70(5):742-50 (2011).

Braun et al., Oligonucleotide and plasmid DNA packaging into polyoma VP1 virus-like particles expressed in coli Biotechnol. Appl. Biochem. vol. 29, pp. 31-43 (1999).
Brennan, D.C., et al.; "Incidence of BK with tracrolimus versus cyclosporine and impact of preemptive immunosuppression reduction"; American Journal of Transplantation 200503 DK, vol. 5, No. 3, pp. 582-594 (2005).
Brocke et al., "Antibodies to CD44 and Integrin a4, but not L-selection, Prevent Central Nervous System Inflammation and Experimental Encephalomyelitis by Blocking Secondary Leukocyte Recruitment," Proc. Natl. Acad. Sci., 96:6896-6901 (1999).
Brown, "Natalizumab in the treatment of multiple sclerosis," Therapeutics and clinical Risk Management, vol. 6, pp. 585-594 (2009).
Brück et al., "Inflammatory Central Nervous System Demyelination: Correlation of Magnetic Resonance Imaging Findings with Lesion Pathology," Ann. Neurol., 42:783-793 (1997).
Calabresi et al., The incidence and significance of anti-natalizumab antibodies: results from AFFIRM and Neurology, vol. 69(14),pp. 1391-1403 (2007).
Cannella, B. and Raine, D.S., "The Adhesion Molecule and Cytokine Profile of Multiple Sclerosis Lesions," Ann. Neurol., vol. 37, pp. 424-435 (1995).
Carter et al., "Lack of Serologic Evidence for Prevalent Simian Virus 40 Infection in Humans," Journal of the National Cancer Institute, vol. 95(2), pp. 1522-1530 (2003).
Casal J I: "Use of the baculovirus expression system for the generation of virus-like particles.", Biotechnology & Engineering Reviews 2001, vol. 18, pp. 73-87 (2001).
Chabas et al., "The Influence of the Proinflammatry Cytokine, Osteopontin, on Augtoimmune Demyelinating Disease," Science, vol. 294, pp. 1731-1735 (2001).
Chang et al., "Self-assembly of the JC virus major capsid protein, VP1, expressed in insect cells", Journal of Virology, vol. 78, pp. 1435-1439 (1997).
Chang et al., "High incidence of JC viruria in JC-seropositive older individuals," J. Neurovirol., vol. 8, pp. 447-451 (2002).
Chaudhuri, A. "Lessons for clinical trials from natalizumab in multiple sclerosis", BMJ, 332:416419 (2006).
Christensen et al., "α4 Integrin Directs Virus-Activated CD8+ T Cells to Sites of Infection," J. Immunol., vol. 154, pp. 5293-5301 (1995).
Ciccarelli, O. and Miller, D. H., "Magnetic resonance imaging in multiple sclerosis", Practical Neurology, vol. 2, pp. 103-112 (2002).
Clifford et al., "HAART Improves Prognosis in HIV-associated Progressive Multifocal Leukoencephalopathy," Neurology, 52:623-625 (1999).
Cohen et al., "A ohase 2 study of natalizymab in subjects with moderate to severe rheumatoid arthritis." ACR Annual Meetings; 10.-15 Washington. Poster 497 Nov. 2006.
Collazos, "Opportunistic Infections of the CNS in Patients with AIDS," CNS Drugs, 17:869887 (2003).
Crowder et al., "Successful Outcome of Progressive Multifocal Leukoencephalopathy in a Renal Transplant Patient," American Journal of Transplantation, 5:1151-1158 (2005).
Delos et al., "Expression of Polyomavirus Minor Capsid Proteins VP2 and VP3 in *Escherichia coli*: In Vitro Interactions with Recombinant VP1 Capsomeres," J. of Virology, vol. 69, No. 12, pp. 7734-7742 (1995).
Demeter, "JC, BK, and Other Polyomaviruses; Progressive Multifocal Leukoencephalopathy," Mandell, Douglas and Bennett's Principles and Practice of Infectious Diseases, Mandell et al. Eds., 4th Ed., New York, NY: Churchill Livingstone; 1995:1400-1406.
Dobbs et al., "Performance characteristics of the immunoglobulin G-capture BED-enzyme immunoassay, an assay to detect recent human immunodeficiency virus type 1 seroconversion," Journal of Clinical Microbiology, vol. 42, No. 6, pp. 2623-2628 (2004).
Dore-Duffy et al., "Expression of Endothelial Cell Activation Antigens in Microvessels from Pateints with Multiple Sclerosis," Frontiers in Cerebral Vascular Biology: Transport and Its Regulation, Plenum, pp. 243-248 (1993).
Dörries et al., "Infection of Human Polyomaviruses JC and BK in Peripheral Blood Leukocytes from Immunocompetent Individuals," Virology, 198:59-70 (1994).

(56) References Cited

OTHER PUBLICATIONS

Dubois et al., "Detection of JC Virus DNA in the Peripheral Blood Leukocytes of HIV-infected Patients," AIDS 10:353-358 (1996).
Dörries et al., "Association of Human Polyomavirus JC with Peripheral Blood of Immunoimpaired and Healthy Individuals," Journal of NeuroVirology, 9(suppl. 1);81-87 (2003).
Dubois et al., "Prevelance of JC Virus viraemia in HIV-infected patients with or without neurolgoical discorders: a prospective study", J of NeuroVirology, vol. 4, pp. 536-544 (1998).
Durez et al., Arthiritis Rheum., "Safety of Combination of Methotrexate (MTX) and Inflizimab (IFX) in a Large Legian Observational Patient Cohort with Refractory Rheumatoid Arthritis," vol. 46, No. 9S, p. 536 (2002).
Dworkin, "A Review of Progressive Multifocal Leukoencephalopathy in Persons With and Without AIDS," Curr. Clin. Top. Infect. Dis. 22:181-195 (2002).
Egli et al., "Prevalence of polyomavirus BK and JC infection and replication in 400 healthy blood donors", J. Infect 199:837-846, (2009).
Elices et al., "VCAM-1 on Activated Endothelium Interacts with the Leukocyte Integrin VLA-4 at a Site Distinct from the VLA-4/Fibronectin Binding Site," Cell, vol. 60, pp. 577-584 (1990).
Elphick et al., "The Human Polyomavirus, JCV, Uses Serotonin Receptors to Infect Cells," Science, vol. 306, pp. 1380-1383 (2004).
"The Encyclopedia of Blindness and vision impairment", 2nd Edition, 2002, Sardgna, Jill, and Otis, T. Paul, (2002).
Engelhardt, et al. "Therapeutic targeting of a4-integrins in chronic inflammatory diseases: tipping the scales of risk towards benefit?" Eur. J. Immunol., 35:2268-2273 (2005).
Engels et al., "Antibodies to JC and BK viruses among persons with non-Hodgkin lymphoma." Int. J. Cancer, vol. 117, pp. 1013-1019 (2005).
Enns et al., "Safety, Tolerability and Immunogenicity of Natalizumab in a Phase III Study of Active Crohn's Disease Therapy," Gastroenterology 126 (4, Suppl. 2): pA462 Apr. 2004.
Ernst et al., "Progressive Multifocal Leukoencephalopathy and Human Immunodeficiency Virus-associated White Matter Lesions in AIDS: Magnetization Transfer MR Imaging," Radiology 210:539-543 (1999).
Fedele et al., "Identical rearranged forms of JC polyomavirus transcriptionial control region in plasma and cerebrospinal fluid of acquired immunodeficiency syndrome patients with progressive multifocal leukoencephalopathy", J of NeroViology, vol. 9, pp. 551-558 (2003).
Ferguson et al., "Axonal damage in acute multiple sclerosis lesions," Brain, vol. 120, pp. 393-399 (1997).
Ferrante et al., "Detection of JC Virus DNA in Cerebrospinal Fluid from Multiple Sclerosis Patients," Multiple Sclerosis, 4:49-54 (1998).
Food and Drug Administration Label for Tysabri®—Revised May 24, 2013.
Foley, J., "Central Visual Disturbances", Developmental Medicine and Child Neurology, vol. 29, pp. 110-112—(1987).
Fox et al., "Advances in the management of PML: Focue on natalizumab," Cleveland clinic J. of Med., vol. 78(2), S33-S37 (2011).
Garrels et al., "Progressive Multifocal Leukoencephalopathy: Clinical and MR Response to Treatment," Am. J. Neuroradiol., vol. 17, pp. 597-600 (1996).
Geschwind et al., "The Relative Contributions of HAART and Alpha-interferon for Therapy of Progressive Multifocal Leukoencephalopathy in AIDS," J. Neurovirol. 7:353-357 (2001).
Gibson et al., "Detection of JC Virus DNA in the Cerebrospinal Fluid of Patients With Progressive Multifocal Leukoencephalopathy," J. Med. Virol. 39:278-281 (1993).
Gillespie et al., Progressive Multifocal Leukoencephalopathy in Persons Infected with Human Immunodeficiency Virus, San Francisco, 1981-1989, Annals of Neurology, vol. 30, No. 4, pp. 597-604 (1991).
Goelz et al., "Assay design and sample collection can affect anti-John Cunningham virus antibody detection." Ann. Neurol., vol. 69, No. 2 pp. 429-431 (2011).
Gold et al., "Expert opinion: Guidelines for the use of natalizumab in multiple sclerosis patients previously treated with immunomodulating therapies," J. of Neuroimmunology, vol. 187, pp. 156-158 (2007).
Goldman, et al., "Molecular cloning and expression of major structural protein VP1 of the human polyomavirus JC virus: formation of virus-like particles useful for immunological and therapeutic studies" Journal of Virology, vol. 73, No. 5, pp. 4465-4469 (1999).
Gorelik et al., "Anti-JC virus antibodies: implications for PML risk stratification." Am. Neurol. Assoc. 2010, vol. 68, pp. 295-303.
Harlow, et al., Using Antibodies: A Laboratory Manual: Portable Protocol I. Cold Spring Harbor Laboratory, Chapter p. 567-569 (Dec. 1, 1998).
Hemler et al., "VLA Proteins in the Integrin Famiy: Structures, Functions, and Their Role on Leukocytes," Annu. Rev. Immunol., vol. 8, pp. 365-400 (1990).
Henson et al., "Amplification of JC Virus DNA from Brain and Cerebrospinal Fluid of Patients with Progressive Multifocal Leukoencephalopathy," Neurology 41: 1967-1971 (1991).
Hernandez et al., "Treatment options for AIDS patients with progressive multifocal leukoencephalopathy", Expert Opin. Pharmacother. vol. 10(3), pp. 403-416 (2009).
Hijazi et al., "Pharmacokinetics, Safety, and Tolerability of R411, a Dual a4131-a4137 Integrin Antagonist After Oral Administration at Single and Multiple Once-Daily Ascending Doses in Healthy Volunteers," J. Clin. Pharmacol., 44:1368-1378 (2004).
Hochberg, "A Sharper Bonferroni Procedure for Multiple Tests of Significance," Biometrika 75:800-802 (1988).
Hoe et al., "JC Virus Can Infect Human Immune and Nervous System Progenitor Cells: Inprications for Pathogenesis", Polyomaviruses and Human Diseases, Chapter 19, edited by Ahsan, Nasimul, pp. 266-273 (2006).
Hoffmann et al., "Progressive Multifocal Leucoencephalopathy with Unusual Inflammatory Response During Antiretroviral Treatment," J. Neurol. Neurosurg. Psychiatry 74:1142-1144 (2003).
Hoffman et al., PML-Falle unter Natalizumab (Tysabri)—(2005).
Hohlfeld et al., "Basic Principles of Immunotherapy for Neurologic Diseases," Seminars in Neurology, vol. 23, pp. 121-131 (2003).
Holman et al., Progressive Muutifocal Leukoencephalopathy in the United States, 1979-1994: Increased Mortality Associates with HIV Infection, Neuroepidemiology, vol. 17, pp. 303-309 (1998).
Hong et al., "Simple quantitative live cell and anti-idiotypic antibody based ELISA for humanized antibody directed to cell surface protein CD20", J of Immunol. Methods, vol. 294, pp. 189-197 (2004).
Hou et al., "JC Virus Can Infect Human Immune and Nervous System Progenitor Cells: Implications for Pathogensis", Polymaviruses and Human Diseases, Retinal Degenerative Diseases: Advances in Experimental Medicine and Biology, Ch. 19, vol. 577, pp. 266-273 (2006).
Hurley et al., "Identification of HIV-Associated Progressive Multifocal Leukoencephalopathy: Magnetic Resonance Imaging and Spectroscopy," J. Neuropsychiatry Clin. Neurosci. 15:1-6 (2003).
Hutchinson, "Natalizumab: A new treatment for relapsing remitting multiple sclerosis", Therapeutics and Clinical Risk Management, vol. 3, No. 2, pp. 259-268 (2007).
IFNB Multiple Sclerosis Study Group, "Interferon Beta-lb is Effective in Relapsing-Remitting Multiple Sclerosis. I. Clinical Results of a Multicenter, Randomized, Double-blind, Placebo-controlled Trial,"Neurology 43:655-661 (1993).
IFNB MS Study Group, Neutralizing antiodbies during treatment of multiple sclerosis with interferon beta-lb: Experience during the first three years, Neurology, vol. 47, pp. 889-894 (1996).
Isaac et al., "Multiple Sclerosis: A Serial Study Using MRI in Relapsing Patients," Neurology 38:1511-1515(1988).
Issekutz, Thomas B., "Lymphoctye homing to sites of inflammation," Curr. Opin. Immunol., vol. 4, pp. 287-293 (1992).

(56) References Cited

OTHER PUBLICATIONS

Jacobs et al., "Intramuscular Interferon Beta-la for Disease Progression in Relapsing Multiple Sclerosis," Annals of Neurology, 39:285-294 (1996).
Jilek at al.: "Immune responses to JC virus in patients with multiple sclerosis treated with natalizumab: a cross-sectional and longitudinal study", Lancet Neurology, vol. 9, pp. 264-272 (2010).
Johnson et al., "Copolymer 1 Reduces Relapse Rate and Improves Disability in Relapsimg-Remitting Multiple Sclerosis: Results of a Phase III Multicenter, Double-blind, Placebo-controlled Trial", Neurology 45:1268-1276 (1995).
Kappos et al., "Predictive Value of Gadolinium-enhanced Magentic Resonance Imaging for Relapse Rate and Changes in Disability or Impairment in Multiple Sclerosis: A Meta-analysis," Lancet, 353:964-969 (1999).
Kappos et al., "Neutralizing antidobies and efficacy of interferon β-1a", Neurology, vol. 65, pp. 40-47 (2005).
Kent et al., "A Monoclonal Antibody to a4 Integrin Suppresses and Reverses Active Experimental Allergic Encephalomyelitis," J. Neuroimmunol. 58:1-10 (1995).
Khatri et al., ""Plasma Exchange Accelerates the Decline of Serum Natalizumab Concentration in Patients with Multiple Results of the Natalizumab PLEX Study"", Neurology, 70, pp. A227-A228, (2008).
Khatri, et al., 60th Annual Meeting of American Academy of Neurology, Chicago, Apr. 2008.
Khatri, et al., "Effect of plasma exchange in accelerating natalizumab clearance and restoring leukocyte function", vol. 72. No. 5, pp. 402-409 (2009).
Khoury et al., "Longitudinal MRI in Multiple Sclerosis: Correlation Between Disability and Lesion Burden," Neurology 44:2120-2124 (1994).
Kieseier et al., "Current disease-modifying therapies in multiple sclerosis," Seminars in Neurology, vol. 23, pp. 133-146 (2003).
Kitamura et al., "High Incidence of Urinary JC Virus Excretion in Nonimmunosuppressed Older Patients," J. Infect. Dis. 161:1128-1133 (1990).
Kleinschmidt-Demasters et al., "Progressive Multifocal Leukoencephalopathy Complicationg Treatment with Natalizumab and Interferon Beta-la for Multiple Sclerosis," N. Engl. J. Med. 353:369-374 (2005).
Knowles et al., "The JC Virus Antibody Response in Serum and Cerebrospinal Fluid in Progressive Multifocal Leucoencephalophy," Journal of Clinical and Diagnostic Virology, 4:183-194 (1995).
Knowles et al., "Prevalence of Long-Term BK and JC Excretion in HIV-Infected Adults and Lack of Correlation With Serological Markers," J. Med. Virol. 59:474-479 (1999).
Knowles et al., "Comparison of cell culture-grown JC virus (primary human fetal glial cells and the JCI cell line) and recombinant JCV VP1 as antigen for the detection of anti-JCV antibody by haemagglutination inhibition," J. Virol. Methods, vol. 109, pp. 47-54 (2003).
Knowles et al., "Population-based study of antibody to the human polyomaviruses BKV and JCV and the Simian polyomavirus SV40." J. Med. Virol., vol. 71, pp. 115-123 (2003).
Knowles, Wendy, "Discovery and Epidemiology of the Human Polyomaviruses BK Virus (BKV) anf JC Virus (JCV)", Polymaviruses and Human Diseases, Ch. 2, pp. 19-45 (2006).
Koralnik, "New Insights Into Progressive Multifocal Leukoencephalopathy," Current Opinion in Neurology, 17:365-370 (2004).
Koren et al., "Recommendations on risk-based strategies for detection and characterization of antibodies biotechnology products" Journal of Immunological Methods, vol. 333,Nr:1-2,pp. 1-9 (2008).
Kornek et al., "Multiple Sclerosis and Chronic Autoimmune Encephalomyelitis—A Comparative Quantitative Study of Aconal Injury in Active, Inactive, and Remyelinated Lesions," Amer. J. Pathalogy, vol. 157, No. 1, pp. 267-276 (2000).
Kozovska et al., "Interferon Beta Induces T-helper 2 Immune Deviation in MS," Neurology 53:1692-1697 (1999).

Kromidas, S., "Validation in analytics," Wiley-VCH Verlag, Apr. 1999, pp. 176-181, 250-251.
Labrijin et al., "Therapeutic IgG4 antibodies engage in Fab-arm exchange with endogenous human IgG4 in vivo", Nature Biotechnology, vol. 27, No. 8, pp. 767-773 (2009).
Langer-Gould et al., "Progressive Multifocal ALeukoencephalopathy in a Patient Treated with Natalizumab," N. Eng. J. Med. 353:375-381 (2005).
Lee et al., "A second-generation ELISA (STRATIFY JCV™ DxSelect™) for detection of JC virus antibodies in human serum and plasma to support progressive multifocal leukoencephalopathy risk stratification", Journal of Clinical Virology, vol. 57, pp. 141-146 (2013).
Lima, Marco A. and Koralnik, Igor J., "New features of progressive multifocal leukoencephalopathy in the era of highly active antiretroviral therapy and natalizumab", J of NeuroViorlogy, vol. 11(suppl. 3), pp. 52-57 (2005).
Ling et al., "The dynamics of herpesvirus and polyomavirus reactivation and shedding in healthy adults: a 14-month longitudinal study." J. Infect. Diseases, vol. 187, pp. 1571-1580 (2003).
Lobb, R.R. and Hemler, M.E., "The Pathophysiologic Role of α4 Integrins In Vivo," J. Clin. Invest., vol. 94, pp. 1731-1735 (1994).
Lundstig, Annika, and Dilner, Joakim, et al., "Serological Diagnosis of Human Polymavirus Infection", Polymaviruses and Human Diseases, Ch. 7, pp. 96-101 (2006).
Major, "Progressive Multifocal Leukoencephalopathy in Patients on Immunomodulatory Therapies", Annu. Rev. Med. (2010), Aug. 31, 2009, Epub ahead of print.
Mamidi et al., "Central Nervous System Infections in Individuals with HIV-I Infection," J. Neurovirol. 8:158-167 (2002).
Manji, H. and Miller, R.F., "Progressive multifocal leucoencephalopathy: progress in the AIDS era," J. of Neurosurgery & Psychiatry, vol. 69, pp. 569-571 (2000).
McDonald et al., "Recommended Diagnostic Criteria for Multiple Sclerosis: Guidelines from the International Panel on the Diagnosis of Multiple Sclerosis," Ann. Neurol., 50:121-127 (2001).
McFarland et al., "The Role of MRI as a Surrogate Outcome Measure in Multiple Sclerosis," Multiple Sclerosis 8:40-51 (2002).
McGuire et al., "JC Virus DNA in Cerebrospinal Fluid of Human Immunodeficiency Virus-infected Patients: Predictive Value for Progressive Multifocal Leukoencephalopathy", Annals of Neurology, vol. 37, No. 3, pp. 395-399 (1995).
Miller et al., "A Controlled Trial of Natalizumab for Relapsing Multiple Sclerosis," N. Engl. J. Med. 348:15-23 (2003).
Miller D H: "Colloquium C15: Natalizumab (anti-VLA4 antibody) in multiple sclerosis", Journal of Neurochemistry, Wiley Interscience, New York, NY, US, vol. 85, No. Suppl. 1, Jan. 1, 2003, p. 96, C15-04.
Millipore, "Short Guide for Developing Immunochromatographic Test Strip", (1996).
Mire-Sluis et al., "Recommendations for the design and optimization of immunoassays used in the detection of host antibodies against biotechnology products," Journal of Immunological Methods, vol. 289, pp. 1-16 (2004).
Molyneux et al., "Correlations between Monthly Enhanced MRI Lesion Rate and Changes in T2 Lesion Volume in Multiple Sclerosis," Ann. Neurol., 43:332-339 (1998).
Montross et al.: Nuclear Assembly of Polyomavirus Capsids in Insect Cells Expressing the Major Capsid Protein Journal of Virology (Sep. 1991), vol. 65, No. 9, pp. 4991-4998.
Niino et al., "Natalizumab Effects on Immune Cell Responses in Multiple Sclerosis", Annals of Neurology, vol. 59, No. 5, pp. 748-754 (2006).
Olsen et al., "White Matter Disease in AIDS: Findings at MR Imaging," Radiology 169:445-448 (1988).
O'Neille, "Expression of vascular addressins and ICAM-1 by endothelial cells in the spinal cord during chronic relapsing experimental allergic encephalomyelitis in the Biozzi AB/H mouse," Immunology, vol. 72, pp. 520-525 (1991).
Oriordan et al., "The prognostic value of brain MRI in clinically isolated syndromes of the CNS," Brain, vol. 121, pp. 495-503 (1998).

(56) References Cited

OTHER PUBLICATIONS

Ou et al.: "The major capsid protein, VP1, of human JC virus expressed in *Escherichia coli* is able to self-assemble into a capsid-like particle and deliver exogenous DNA into human kidney cells", Journal of General Virology, vol. 80, pp. 39-46 (1999).

Padgett et al., "Prevalence of antibodies in human sera against JC virus, an isolate from a case of progressive leukoencephalopathy", J. Infect. Dis. 127:467-70 (1973).

Padgett et al., "Virologic and Serologic Studies of Progressive Multifocal Leukoencephalopathy," Prog. Clin. Biol. Res. 105:107-117 (1983).

Palkhivala, Alison, "A Case of PML in a Natalizumab-Treated MS Patient", Sep. 22, 2008, downloaded from www.medscape.com on Apr. 2, 2021.

Patton et al., "An acid dissociation bridging ELISA for detection of antibodies directed against therapeutic proteins in the presence of antigen", Journal of Immunological Methods, vol. 304, pp. 189-195 (2005).

Pestalozza et al., "Monthly brain magnetic resonance imaging scans in patients with clinically isolated syndrome," Multiple Sclerosis, vol. 11, pp. 390-394 (2005).

Petterson et al., "VCAM-1-Positive Microglia Target Oligodendrocytes at the Border of Multiple Sclerosis Lesions," J. Neuropathy Exp. Neurol., vol. 61, No. 6, pp. 539-546 (2002).

Piccinni, et al., "Stronger association of drug-induced progressive multifocal leukoencephalopathy (PML) with biological immunomodulating agents", Eur. J. Clin. Pharmacol. 66:199-206 (2010).

Plavina et al., "Multi-site analytical validation of an assay to detect anti-JCV antibodies in human serum and plasma", J. Clinical Viorlogoy, vol. 53, p. 65-71 (2012).

Plavina et al., "Anti-JCV antibody index further defines PML risk in natalizumab-treated MS pateients," The 27th Annual Meeting of the Corsortium of Multiple Sclerosis Centers Acknowledgements, Accessed March Neurology, Warnke C J Neurol Neurosurg Psychiartry Ann Neurol, May 30, 2013, pp. 1736-1742.

Plavina et al., Serum Concentration of Natalizumab, Endogenous IgG4, and sVCAM-1 in Natalizumab-Treated PML Patients (P05.159), Neurology, vol. 80 (7 Supplement), 2013).

Polman et al., "A Randomized, Placebo-Controlled Trail of Natalizumab for Relapsing Multiple Sclerosis," N. Engl. J. Med., 354(9):899-910 (2006).

Post et al., "Progressive Multifocal Leukoencephalopathy in AIDS: Are There Any MR Findings Useful to Patient Management and Predictive of Patient Survival?," Am. J. Neuroradiol. 20:1896-1906 (1999).

PRISMS Study Group, "Randomised Double-blind Placebo-controlled Study of Interferon 13-la in Relapsing/Remitting Multiple Sclerosis," Lancet 352:1498-1504 (1998).

PRISMS Study Group, "PRIMSMS-4: Long-term efficacy of interferon-β-1a in relapsing MS," Neurology, vol. 56, pp. 1628-1636, , (2001).

Przepiorka et al., "Successful Treatment of Progressive Multifocal Leukoencephalopathy with Low-Dose Interleukin-2," Bone Marrow Transplant, 20:983-987 (1997).

Public Health Advisory—Suspended Marketing of Tysabri (Natalizumab), Feb. 28, 2005.

Raffel et al., "Assay Selction Affects John Cunningham Virus Serostatus Classification in Multiple Sclerosis," Annals of Neurology vol. 72, No. 2, pp. 295-296 (2012).

Raine et al., "Homing to Central Nervous System Vasculature by Antigen-Specific Lymphocytes—II. Lyphocyte/Endothelical Cell Adhesion during the Intitial Stages of Autoimmune Demyelination," Lab Invest. vol. 63, No. 4, pp. 476-489 (1990).

Rankin et al., "Progressive Multifocal Leukoencephalopathy in a Pateitn with Rheumatoid Arthritis and Polymyositis," J. Rheumatol, vol. 22, pp. 777-779 (1995).

Redington et al., "Viral Infections of the Nervous System, 2002," Arch. Neurol: 59:712-718 (2002).

Rep et al., "Recombinant Interferon-B Blocks Proliferation but Enhances Interleukin-10 Secretion by Activated Human T-Cells," J. Neuroimmunol. 67:111-118 (1996).

Rispens et al., "Measurement of serum levels of natalizumab, an immunoglobulin G4 therapeutic monoclonal antibody", Analytical Biochemistry, vol. 411, pp. 271-276 (2011).

Rollison Dana E et al.: ""Prediagnostic circulating antibodies to JC and BK human polyomaviruses and risk of non-Hodgkinlymphoma."", Cancer Epidemiology, Biomarkers & Prevention : A Publication of the American Association for Cancer Research, Cosponsored By the American Society of Preventive Oncology, vol. 15, No. 3, pp. 543-550 (2006).

Rudick et al., "Incidence and Significance of Neutralizing Antibodies to Interferon Beta-1a in Multiple Sclerosis," Neurology 50:1266-1272 (1998).

Rudick et al., "Natalizumab plus Interferon Beta-1a for Relapsing Multiple Sclerosis," N. Engl. J. Med., 354(9):91 1-923 (2006).

Runmarker, B. and Andersen, O., "Prognostic factors in a multiple sclerosis incidence cohort with twenty-five years of follow-up," Brain, vol. 116, pp. 117-134 (1993).

Sadiq et al., "JCV detection in multiple sclerosis patients treated with natalizumab," J Neurol, vol. 257, pp. 954-958 (2010).

Sailer et al., "Quantitative MRI in patients with clinically isolated syndromes suggestive of demyelination," Neurology, vol. 52, pp. 599-606 (1999).

Salmaggi et al., "Reversal of CSF Positivity for JC Virus Genome by Cidofovir in a Patient with Systemic Lupus Erthematosus and Progressive Multifocal Leukoencephalopathy," Neurol. Sci. 22:17-20 (2001).

Salunke et al., "Polymorphism in the Assembly of Polyomavirus Capsid Protein VP", Biophys Journal, vol. 56, pp. (1989).

Sandborn et al., "Efficacy of Natalizumab in Maintaining Clinical Response and Remission in Crohn's Disease: Comparison of Sustained Response and Remission Rates Through 12 Months Vs Point-In-Time Response and Remission Rates at Month 12," Gastroenterology, vol. 128, No. 4, Suppl. 2, p. A586 (2005).

Sandrock et al.: Risk Stratification for Progressive Multifocal Leukoencephalopathy (PML) in MS Patients: Role of Prior Immunosuppressant Use, Natalizumab-Treatment Duration, and Anti-JCV Antibody Statue, Neurology, vol. No. 9, Suppl. 4, Mar. 2011 (Mar. 2011), p. A248, 63rd Annual Meeting of the American Academy of Neurology; Honolulu, HI, USA; Apr. 9-16, 2011.

Sandrock, et al., "Risk of Natalizumab-Associated Progressive Multifocal Leukoencephalopathy" 25th Annual Meeting the Consortium of Multiple Sclerosis Centers, Jun. 1-4, 2011 Montreal, Quebec, Canada.

Schuurman et al., "Normal human immunoglobulin G4 is bispecific: it has two different antigen-combining sites," Immunology, 97:693-698 (1999).

Seth et al., "Advances in the Biology of JC Virus and Induction of Progressive Multifocal Leukoencephalopathy," J. Neurovirol. 9:236-246 (2003).

Shapiro et al., "Devlelopment and validation of immunoassays to quantify the half-antibody exchange of an IgG4 antibody, natalizumab (Tysabri) with endogenous IgG4", J. Pharm and Biomedical Analysis, vol. 55, pp. 168-175 (2011).

Shitrit et al.,"Progressive Multifocal Leukoencephalopathy in Transplant Recipients," Transpl. Int. 17:658-665 (2005).

Simon et al., "A Longitudinal Study of T1 Hypointense Lesions in Relapsing MS," Neurology 55:185-192 (2000).

Sponzilli et al., Progressive multifocal leukoencephalopath: A complication of immunosuppressive treatment, Neurology, vol. 25, pp. 664-668 (1975).

Springer, Timothy A., "Traffic Signals for Lymphocyte Recirculation and Leukocyte Emigration: The Multistep Paradigm," Cell, vol. 76, pp. 301-314 (1994).

Steffen et al., "Evidence for Involvement of ICAM-1 and VCAM-1 in Lymphocyte Interaction with Endothelium in Experimental Autoimmune Encephalomyelitis in the Central Nervous System in the SJL/J Mouse," Amer. J. Pathology, vol. 145, No. 1, pp. 189-201 (1994).

(56) References Cited

OTHER PUBLICATIONS

Steinman, Lawrence, "Blocking adhesion molecules as therapy for multiple sclerosis: natalizumab," Nature Reviews. Drug Discovery, Nature Publishing Group, GB, vol. 4, No. 6, pp. 510-518 (2005).
Stolt et al.: "Seroepidemiology of the human polyomaviruses", Journal of General Virology (2003), vol. 84, pp. 1499-1504.
Stone, John H., "IgG4-related disease: pathophysiologic insights drive emerging treatment approaches," Clin. Exp. Rheumatol. vol. (Suppl 98), pp. 1-3 (2016).
Stuve, et al., "Potential Risk of Progressive Multifocal Leukoencephalopathy With Natalizumab Therapy", Arch vol. 64, (Feb. 2007). p. 9 169-176.
Subramanyam et al.: "Anti-JCV Antibodies Are Consistently Detected Prior to and after PML Diagnosis in Natalizumab-Treated MS Patients", Neurology, vol. 76, No. 9, Suppl. 4, Mar. 2011 (Mar. 2011), pp. A636-A637, 63rd Annual Meeting of the American Academy of Neurology; Honolulu, HI, USA; Apr. 9-16, 2011.
Sundsfjord et al., "BK and JC Viruses in Human Immunodeficiency Virus Type 1-lnfected Persons : Prevalence, Excretion, Viremia, and Viral Regulatory Regions," J. Infect. Dis. 169:485-490 (1994).
Takada, et al., "The integrins", Genome Biol. 8:215 (2007).
Tantisiriwat et al., "Progressive Multifocal Leukoencephalopathy in Patients with AIDS Receiving Highly Active Antiretroviral Therapy," Clin. Infect. Dis. 28:1152-1154 (1999).
Tenser, R.B. et al., "Natalizumab for Relapsing Multiple Sclerosis," New Engl. J. Med., 354(22): 2387-2389 (2006).
Thompson et al., "Major Differences in the Dynamics of Primary and Secondary Progressive Multiple Sclerosis," Ann. Neurol. 29:53-62 (1991).
Thompson et al., "Serial Gadolinium-Enhanced MR1 in Relapsing/ Remitting Multiple Sclerosis of Varying Disease Duration," Neurology 42:60-63 (1992).
Tornatore et al., "Detection of JC Virus DNA in Peripheral Lymphocytes from Patients with and without Progressive Multifocal Leukoencephalopathy," Ann. Neurol., 31:454-462 (1992).
Trampe et al., "Anti-JC virus antibodies in a large German natalizumab-treated multiple sclerosis cohort," Neurology, vol. 78(22), pp. 1736-1742 (2012).
Trapp et al., "Axonal Transection in the Lesions of Myultiple Sclerosis," N.E. J. of Medicne, vol. 338, pp. 278-285 (1998).
Tur and Montalban, "Natalizumab: Risk Stratification of Individual Patients with Multiple Sclerosis." CNS Drugs, vol. 28, pp. 641-648 (2014).
Vago et al., "JCV-DNA and BKV-DNA in the CNS Tissue and CSF of AIDS Patients and Normal Subjects. Study of 41 Cases and Review of the Literature," J. Acquir. Imm. Defic. Syndr. Hum. Retrovirol. 12:139-146 (1996).
Van Assche et al., "Physiological Basis for Novel Drug Therapies Used to Treat the Inflammatory Bowel Diseases: I. Immunology and therapeutic potential of antiadhesion molecule therapy in inflammatory bowel disease," Am. J. Physiol. Gastrointest. Liver Physiol., 288:G169-G174 (2005).
Van Assche, "Progressive Multifocal Leukoencephalopathy After Natalizumab Therapy for Crohn's Disease", The New England Journal of Medicine, vol. 353, No. 4, pp. 362-368, (2005).
Verbeeck J et al.: "JC viral loads in patients with Crohn's disease treated with immunosuppression: can we screen for elevated risk of progressive multifocal leukoencephalopathy?", Gut vol. 57, No. 10, Oct. 2008.
Viscidi, "Serological Cross-Reactivities between Antibodies to Simian Virus 40, BK Virus, and JC Virus Assessed by Virus-Like-Particle-Based Enzyme Immunoassays", Clinical and Diagnostic Laboratory Immunology, vol. 10, No. 2, pp. 278-285, (2003).
Von Andrian et al., "a4 Integrins as Therapeutic Targets in Autoimmune Disease" N. Engl. J. Med., 348(1):68-72 (2003).
Waknine, Yael, "Tysabri Suspended From U.S. Market", Feb. 28, 2005, downloaded from www.medscape.com on Apr. 6, 2021.
Warnke et al.: "Natalizumab and progressive multifocal leukoencephalopathy: what are the causal factors and can it be avoided?", Archives of Neurology, vol. 67, No. 8, Aug. 1, 2010 (Aug. 1, 2010), pp. 923-930.
Washington et al., "Expression of Immunologically Relevant Endothelial Cell Activation Antigens on Isolated Central Nervous System Microvessels from Patients with Multiple Sclerosis," Ann. Neurol., vol. 35, pp. 89-97 (1994).
Weber et al., "Progressive Multifocal Leukoencephalopathy Disgnosed by Amplification of JC Virus-specific DNA from Cerebrospinal Fluid," AIDS 8:49-57 (1994).
Weber et al., "Specific Diagnosis of Progressive Multifocal Leukoencephalopathy by Polymerase Chain Reaction," J. Infect. Dis. 169:1138-1141 (1994).
Weber T et al.: "Analysis of the systemic and intrathecal humoral immune response in progressive multifocal leukoencephalopathy.", The Journal of Infectious Diseases vol. 176, No. 1, Jul. 1997 pp. 250-254.
Wenning, et al., Treatment of Progressive Multifocal Leukoencephalopathy Associated with Natalizumab, N Engl J Med, vol. 361. No. 11. (Sep. 10, 2009), p. 1075-1080.
Whitaker et al., "Outcomes Assessment in Multiple Sclerosis Clinical Trials: a Critical Analysis," Multiple Sclerosis, 1:37-47 (1995).
Willoughby et al., "Serial Magnetic Resonance Scanning in Multiple Sclerosis: A Second Prospective Study in Relapsing Patients," Ann. Neurol., 25:43-49 (1989).
Wright et al., "Standardisation and validation of enzyme-linked immunosorbent assay techniques for the detection of antibody in infections disease diagnosis," Rev. Sci. Tech. Off. Int. Epiz., vol. 12(2), pp. 435-450 (1993).
Yednock et al., "Prevention of Experimental Autoimmune Encephalomyelitis by Antibodies Against a4131 Integrin," Nature 356:63-66 (1992).
Yousry et al., "Evaluation of Patients Treated with Natalizumab for Progressive Multifocal Leukoencephalopathy," New England Journal of Medicine, vol. 354: 924-933 (2006).
Yu et al., "How Natalizumab Binds and Antagones a4 Integrins*", J of Bioglogical Chemistry, vol. 288, No. 45, pp. 32314-32325 (2013).
Zang et al., "Regulation of Chemokine Receptor CCR5 and Production of RANTES and MIP-Ia by Interferon-B," J. Neuroimmunol. 112:174-180 (2001).

\* cited by examiner

ASSAY FOR JC VIRUS ANTIBODIES

RELATED APPLICATIONS

This application claims the benefit of U.S. Provisional Application No. 61/294,048, filed Jan. 11, 2010, and U.S. Provisional Application No. 61/316,193, Mar. 22, 2010, both of which are incorporated herein by reference in their entirety.

FIELD OF THE INVENTION

The invention relates to methods and reagents for analyzing samples for the presence of JC virus antibodies.

BACKGROUND

Progressive Multifocal Leukoencephatopathy (PML) is an opportunistic infection of the central nervous system (CNS) that associated with exposure to the JC virus (JCV), a polyoma virus that is be to be pathogenic in humans only under conditions of persistent immune suppression or immune modulation. While the presence of JCV is required for development of PML, PML risk is considered, in a not well-understood way, to be associated with the convergence of multiple viral and host-related factors that cause the virus to become pathogenic (Major, "Progressive Multifocal Leukoencephalopathy in Patients on Immunomodulatory Therapies" *Annu. Rev. Med* 61:35-47 (2010) [2009 Aug. 31, Epub ahead of print]). Published studies reporting the prevalence of JCV infection in the human population are varied. This information is based on various types of studies including PCR analysis for viral DNA and detection of antibodies to JCV. Despite the prevalence of JCV in the population, infection with JCV rarely results in PML, even in individuals with documented immunosuppression.

Published reports on JCV DNA detection suggest the method to be insensitive and of limited use for assessing exposure to JCV because JCV DNA has been rarely and inconsistently detected in the plasma, serum or peripheral blood mononuclear cells of JCV-infected PML patients. Detection of anti-JCV antibodies appears to be a more sensitive marker of JCV infection; however the reported results are variable. In 1973, Padgett and Walker published a study reporting a JCV seroprevalence of 65-84% using a haemagglutination inhibition (HI) assay (Padgett and Walker, "Prevalence of antibodies in human sera agains JC virus, an isolate from a case of progressive multifocal leukoencephalopathy" *J. Infect. Dis.* 127:467-70, 1974. Later reports of JCV seroprevalence rates using the HI assay or ELISA have varied between 33-91%. The variable seroprevalence rates among these studies are likely due to marked differences in the size and demographics of the studies, and, perhaps most importantly, differences in assay methods.

It is therefore desirable to implement a reliable and sensitive assay for determining the presence of JCV antibodies that can be used, for example, for assessing whether an individual has been exposed to JCV.

SUMMARY OF THE INVENTION

The invention relates to the development of an analytically validated sensitive assay for detecting the presence of JCV antibodies in a biological fluid, serum or plasma.

Accordingly, the invention relates to a method that includes obtaining a biological sample from a subject (e.g., plasma, serum, blood, urine, or cerebrospinal fluid (CSF)); contacting the sample with highly purified viral-like particles (HPVLPs) under conditions suitable for binding of a JCV antibody in the sample to an HPVLP; detecting the level of JCV antibody binding in the sample to HPVLP; and correlating the detected level with a reference, such that the reference is selected to indicate a false negative raw not greater than 3% and minimal cross reactivity to other components of the sample such as antibodies against other polyoma viruses, e.g. BK virus (BKV). In some embodiments, the reference, derived from a control sample or set of samples, is processed with the sample from the subject. In some embodiments, the reference is selected such that the false negative rate of the assay is not greater than 1%.

In one embodiment, at least about 10% of the HPVLPs in a preparation of purified HPVLPs contain more than five VP1 polypeptides per HPVLP). In other embodiments, at least about 15%, about 20%, about 25%, about 10%, about 40%, about 50%, about 60%, about 65%, about 70%, about 80% or about 90% of the HPVLPs in a preparation of purified HPVLPs contain more than five VP1 polypeptides per HPVLP.

The assay can be performed such that the HPVLP is immobilized on a solid substrate such as a microtiter plate or slide. In some embodiments, the HPVLP consists essentially of VP1 viral protein. The HPVLP can farther include other viral proteins, for example at least one of a VP2 or a VP3. The viral protein(s) in the HPVLP can be recombinantly derived (e.g., a MAD1 strain VP1) or can be a naturally-occurring viral protein (e.g., derived from a naturally-occurring source). The method can be performed using, for example, a biological sample obtained from a subject currently being heated with an immunomodulatory drug, a subject considering initiating treatment with an immunomodulatory drug, or a subject suspected of having Progressive Multifocal Leukoencephalopathy (PML).

In some aspects, the assay method is a two-step assay that further includes a secondary confirmation assay process that includes contacting a portion of the biological sample from the subject with HPVLP in solution (prior to incubating the sample with the HPVLP attached to a solid substrate), thereby providing a secondary sample; contacting the secondary sample with HPVLP under the same conditions used for the primary assay; detecting the level of JCV antibody binding to HPVLP in the secondary sample; and comparing the detected level of JCV antibody in the secondary sample to the level of JCV antibody in the sample that was not preincubated with soluble HPVLP, such that a decrease in the detected level in the secondary assay sample compared to the sample that was not preincubated indicates the sample is positive for JCV antibody, and a change the detected level below a specified percentage indicates that there is no JCV-specific antibody present in the sample.

An assay described heroin can be used to assay for the presence of JCV antibodies in a subject who has never received treatment with an immunomodulator; or in a subject who has previously received an immunomodulator, but who is no longer receiving treatment with the immunomodulator; or in subject who is presently undergoing treatment with an immunomodulator.

Detection of JCV antibodies binding to the HPVLPs in an assay featured in the invention can indicate that a subject is at an increased risk for PML. Detection of JCV antibodies can also indicate that the subject is at an increased risk for adverse symptoms, such as the development of PML, upon administration of certain therapeutic agents, such as certain immunomodulators, and therefore be subject is not a candidate for treatment with these agent. For example, detection of JCV antibodies in sample from a subject can indicate that the subject is not a candidate for treatment with an anti-VLA-4 therapeutic, such as natalizumab. In certain embodiments, detection of JCV antibodies in a biological sample can indicate that the subject is a candidate for treatment with an immunomodulator, such as natalizumab, except that the subject will undergo enhanced monitoring during treatment than a subject who does not have detectable JVC antibodies. For example, the enhanced monitoring can include observation for adverse symptoms such as symptoms that may indicate the development of PML.

Failure to detect JCV antibodies binding to HPVLPs in an assay featured in the invention can indicate that the subject is a candidate to receive treatment with an immunomodulator, such as natalizumab, and in one embodiment, the subject is further administered the immunomodulator. A subject determined not to have JCV antibodies can be re-tested at least annually (e.g., at least every 3 months, every 6 months, every 9 months, or every 12 months) to determine whether the subject has developed JCV antibodies, which may indicate that the subject has been infected with JCV. A subject who previously did not have detectable JCV antibodies in a biological sample, and who subsequently develops XV antibodies in a biological sample, can stop receiving treatment with an immunomodulator.

In some embodiments, a subject who was previously identified as having JCV antibodies, can be subsequently tested at a later date and determined not to have JCV antibodies. These subjects can be determined to be candidates to receive treatment with an immunomodulator, such as natalizumab. In one embodiment, a subject who previously tested positive for the presence of JCV antibodies and who subsequently tested negative for JCV antibodies can be administered the immunomodulator, and undergo enhanced monitoring as compared to a subject who never tested positive for JCV antibodies, such as to monitor for symptoms that may indicate the development of PML.

An assay featured in the invention is useful to treat a subject having an immunological disease or disorder, such as multiple sclerosis (MS) or Crohn's Disease (CD). In one embodiment, an assay described herein has been validated for use in MS and CD patients, such as by showing that the assay is effective to detect JCV antibodies in MS and CD patients in a controlled test environment, such as in a clinical trial.

In another aspect, the invention relates to a kit comprising an HPVLP and at least one reagent for performing an assay to identify a JCV antibody level in a sample, such as a biological sample.

In other aspects, the invention relates to a solution comprising HPVLP particles consisting essentially of VP1-containing particles that are greater in size than a VP1 pentamer, e.g., containing about 5, 10, 20, 30, 40, 50, 60, 70 or 72 pentamers or containing about 25 VP1 molecules, about 50 VP1 molecules, about 100 VP1 molecules, about 150 VP1 molecules, about 200 VP1 molecules, about 300 VP1 molecules, about 350 VP1 molecules or about 360 VP1 molecules.

Another aspect featured in the invention is a method of preparing a solution of HPVLPs, the method comprising removing VP1-containing particles from the solution that are the size of a VP1 pentamer or less. In one method VP1 polypeptides are expressed in cells, e.g., in insect cells or mammalian cells. The cells are lysed, and then the cells are treated with a nuclease, such as BENZONASE®. Cell debris is removed by precipitation, such as by salt (e.g., ammonium sulfate) precipitation, and then the VP1-containing supernatant is concentrated and further purified using diafiltration, such as by one or two passages through a membrane, e.g., a tangential flow filtration (TFF) membrane. The solution containing the VP1-containing particles, e.g., HPVLPs, is then further purified through an ion-exchange step, and elution of the HPVLPs is performed, e.g., with a buffer. VP1 purity can be assessed, e.g., electrophoresis (e.g., SDS-PAGE) or mass spetometry. The presence of HPVLPs can be confirmed by microscopy, e.g., electron microscopy. The percentage of total protein in the form of HPVLPs can be determined by sedimentation velocity analytical ultracentrifugation.

In one aspect, the invention features a method of identifying a subject at risk of developing PML, such as by obtaining a biological sample from the subject; contacting the biological sample with HPVLPs under conditions suitable for binding of a JC Virus (JCV) antibody in the sample to an HPVLP; detecting the level of JCV antibody binding in the sample to HPVLPs; and correlating the detected level with a reference set, wherein the subject is at increased risk of PML if JCV antibody binding is detected. The reference set is selected to indicate a false negative rate of about 5%, about 3%, about 1% or less.

In another aspect, the invention features a method of identifying PML risk in a subject by determining the level of anti-JCV antibodies in a sample from the subject, such as from a plasma, blood or serum sample; and assigning a risk level to the subject according to the level of anti-JCV antibodies in the sample. The subject may be receiving an immunomodulatory therapy, such as an anti-VLA4 treatment, e.g., natalizumab, or may be a candidate for receiving an immunomodulatory thereapy. In some embodiments, the subject has been diagnosed with an immunological disease or disorder, such as multiple sclerosis or Crohn's disease. In one embodiment, the level of anti-JCV antibodies is determined using a one-step assay, and in another embodiment, the level of anti-JCV antibodies is determined using a two-step assay. Either the one-step assay or the two-step assay may include an ELISA assay.

In one embodiment, the method of identifying PML risk in a subject further includes determining the level of anti-JCV antibodies in the subject in a sample from a date subsequent to the initial sample; comparing the level of anti-JCV antibodies in the sample from the subsequent date to the level in the sample from the initial sample; and determining whether the subject is at increased risk of PML at the subsequent date compared to the time of the initial sample.

In one aspect, the invention features a method of monitoring PML risk in a subject, the method comprising determining the level of anti-JCV antibodies in a subject using a sample from a first date; assigning a risk of PML (e.g., high, or moderate or low risk) based on the level of anti-JCV antibodies in the subject on the first date; determining the level of anti-JCV antibodies in the subject using a sample from a second date; and assigning a risk of PML (e.g., high, or moderate or low risk) based on the level of anti-JCV antibodies in the subject on the second date.

As used herein, an "HPVLP" is a highly purified VLP ("virus-like particle") consisting predominantly of the VP1 protein. An "HPVLP" featured in the invention is composed mainly of the major capsid protein "VP1," which can be a naturally-occurring VP1 or a recombinant VP1, from the polyomavirus, JC Virus (JCV). An HPVLP can be composed of, e.g., more than one pentameric subunit, at least 10 pentameric subunits, at least 20 pentameric subunits, at least 30 pentameric subunits, at least 50 pentameric subunits, at least seventy-two pentameric subunits or more of VP1. An HPVLP may contain VP1 polypeptides in an undetermined configuration (e.g., the polypeptides may or may not be organized in pentamers), in which case an HPVLP can be composed of more than 5 VP1 polypeptides, at least 50 VP1 polypeptides, at least 150 VP1 polypeptides, at least 360 VP1 polypeptides or more. HPVLPs include capsomeres, which contain about 10 to 24 pentamers. An HPVLP featured in the invention can bind antibodies against naturally-occurring, intact JC virus. In some embodiments, an HPVLP includes a second, and optionally a third, type of polypeptide that is a minor capsid protein of JC virus, e.g., at least one VP2 or VP3 polypeptide. The VP2 or VP3 can be recombinant or naturally-occurring or naturally-derived polypeptides.

Such "highly purified" particles contain more than one VP1 pentamer, e.g., at least 5, 10, 20, 30, 40, 50, 60, 70, 72 VP1 pentamers, or less than 100 VP1 pentamers. Such highly purified particles can be obtained, for example, by a method that involves double filtration. For example, in one embodiment, a highly purified preparation of VLPs is obtained by purifying the particles at least twice by centrifugation, e.g., through a sucrose cushion. In general, an HPVLP preparation can be identified by its activity in an ELISA assay using defined control samples. In some cases, such control samples are negative controls and/or control samples containing low levels of JCV antibodies.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
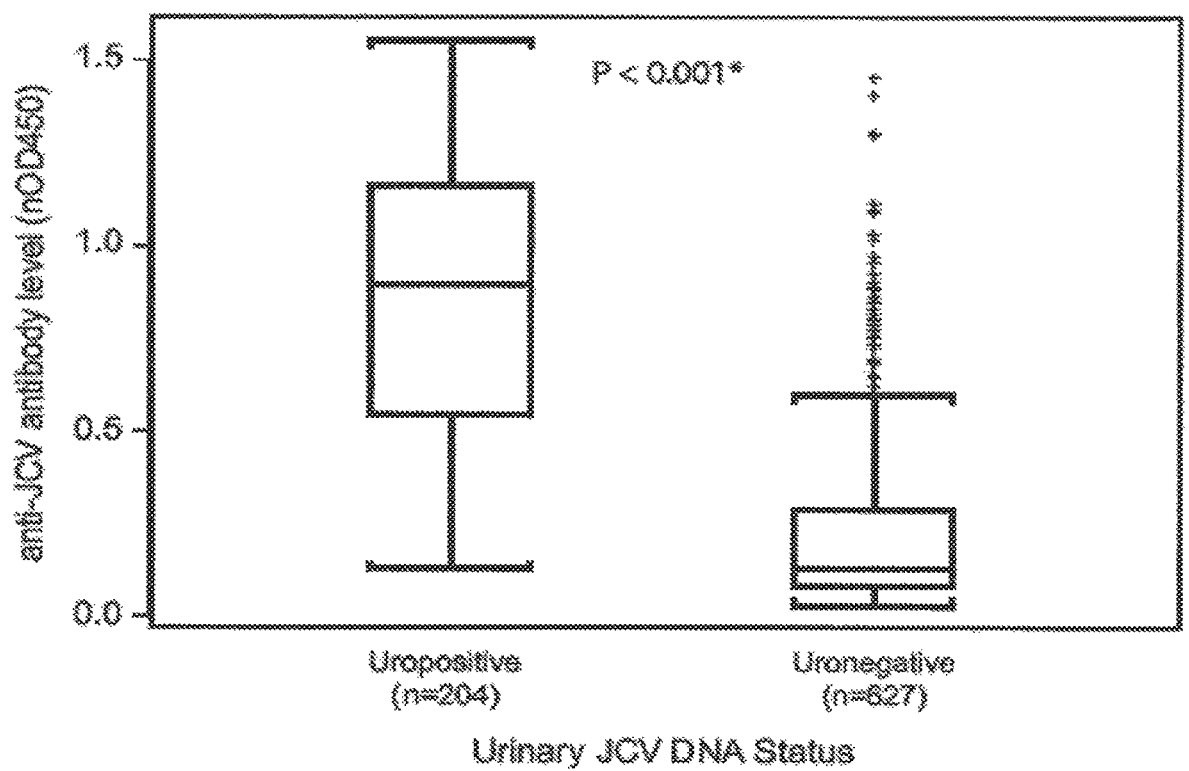
FIG. 1 is a graph depicting the results of an HPVLP ELISA on samples from subjects positive for JCV DNA in their urine (Uropositive) and negative for JCV DNA in their urine (Uronegative). The box represents the interquartile (IQR) range with the median line in the center; brackets represent observations within 1.5 times the IQR. "+" signs represent observations beyond 1.5 times the IQR (outliers). *Mann-Whitney U test.

A sensitive assay for JCV antibodies that minimizes false negatives and minimizes detection of cross-reacting antibodies is useful for identification of individuals that have been exposed to JCV. Deployment of such a test may be useful in the identification of individuals who have a current JCV infection or have had sufficient past exposure to JCV to develop antibodies against the virus. Such an assay may also provide a tool to assist clinicians with PML clinical vigilance and risk stratification. For example, such a test may be useful for practitioners and patients as part of an evaluation of a patient's risk of developing PML by accurately assessing whether a subject has been exposed to JCV. In some cases, the analysis may include determining JCV antibody levels in a biological sample from the patient.

Certain difficulties lie in development of a useful assay for JCV antibodies, for example, the establishment of validated cut points. Applicants have solved this problem using data derived from assays of urine and plasma samples from patients that are uropositive or uronegative for JCV DNA. Another problem is developing an assay with specificity and reproducibility. Applicants have solved this problem by using a highly purified viral protein-containing particle in an antibody assay. In addition, applicants have discovered that the use of a secondary assay to resolve samples with ambiguous results in the primary assay improves the utility of the assay for providing a useful result for such samples.

Accordingly, an analytically validated assay that uses a highly purified VP1-containing virus-like particle (VLP) has been developed to detect the presence of JCV antibody in a body fluid, such as serum, plasma, urine, CSF, or other body fluid that contains antibodies. In experiments to validate the new assay, an approximately 54% prevalence of JCV antibodies in a population of MS patients enrolled in a clinical study was identified. A key feature of the assay described herein is the use of a highly purified viral-like particle (HPVLP).

One advantage of the assay described herein is that it has a relatively low false negative rate, e.g., a false negative rate of about 10%, about 8%, about 6%, about 4%, about 3%, about 1% or less for the detection of antibodies to JCV. In general, the assay has a false negative rate of only about 3% or less for the detection of antibodies to JCV. As described herein the new assay can be used to monitor the seroconversion rate for JCV. For example, the assay has been used to discover an annual seroconversion rate of no more than about 2% in a tested cohort of subjects who were initially negative for JCV antibody. This demonstrates that the assay can be useful for monitoring the JCV exposure status of an individual over time.

The assay can be used for the detection of JCV antibodies in any human subject, including a subject considering treatment with an immunomodulator, for example an anti-VLA-4 therapy (e.g., natalizumab), an anti-CD20 therapy (e.g., rituximab), an anti-CD11 a therapy (e.g., efalizumab), or mycophenolate mofetil; in a subject currently being treated with an immunomodulator; or a subject that has ceased treatment with an immunomodulator. The assay may be useful to others who may be susceptible to PML, such as individuals having lymphoproliferative disorders, such as multiple myeloma or a lymphoma; individuals infected with human immunodeficiency virus (HIV), or having acquired immune deficiency syndrome (AIDS), hematologic malignancies, or an autoimmune disease such as systemic lupus erythematosus (SLE), an inflammatory bowel disease, such as Crohn's Disease (CD) or ulcerative colitis, multiple sclerosis (MS) or arthritis, e.g., rheumatoid arthritis (RA). The assay may also be useful to subjects receiving immunosuppressive or immunomodulatory therapies, such as transplant patients. Exemplary immunosuppressive or immunomodulatory therapies include natalizumab, rituximab, efalizumab, and mycophenolate mofetil. The assay can be useful for detection of JCV antibodies in a subject having a disorder, or being treated with a drug, disclosed in Piccinni et al. "Stronger association of drug-induced progressive multifocal leukoencephalopathy (PML) with biological immunomodulating agents" *Eur. J. Clin. Pharmacol.* 66:199-206, 2010, the contents of which are incorporated herein by reference.

VP1

It was discovered that the use of HPVLPs in an assay for JCV antibodies can improve the accuracy of the assay and is useful in an assay suitable for analytic and diagnostic purposes. VP1 for use in producing HPVLPs can be generated using methods known in the art and can be either naturally-occurring VP1 or recombinantly produced VP1, e.g., a VP1 from a JCV virus. In general, the VP1 used is VP1 from MAD1 strain of JCV. In some embodiments, the VP1 used in the assay comprises VP1 from more than one JCV strain, for example, from one or more of strains 1A, 1B, 2A, 2B, 3, 4, and 7. After preparation of VP1, e.g., recombinantly synthesized VP1, the VP1 for use in the assays described herein is then further purified through standard biochemical methods including density-gradient/ultracentrifugation methods, or a series of chemical precipitation steps, concentration/diafiltration and ion-exchange chromatography. The purification methods typically include a step to remove smaller proteins including monomer VP1 polypeptides, or pentamer VP1. The removal of these smaller particles can be done in, for example, in one step or in two steps (e.g., a first filtration step to remove VP1 monomers, and then a second filtration step to remove pentamer VP1 particles). Such biochemical purification methods are known to those in the art. Examples 1 and 7 provide two different methods of JCV VP1-VLP purification.

An HPVLP preparation (HPVLPs) according to one aspect of the present invention does not contain significant amounts of VP1 monomer (e.g., has been purified to remove monomers). An HPVLP preparation according to another aspect of the present invention does not contain significant amounts of VP1 molecules in configurations the size of a VP1 pentamer, or smaller (including monomer). The HPVLP can be prepared from recombinant VP1 or naturally-occurring VP1 (e.g., isolated from virus or virus capsid). In some embodiments, additional JCV components, such as one or both of the minor coat proteins from JC virus, e.g., VP2 or VP3, are included in the HPVLP particle or are associated with the substrate.

In some cases, recombinantly expressed VP1 may not assemble into pentamers or HPVLPs that resemble naturally-occurring viral capsids, for example, recombinantly expressed VP1 may assemble into tubes or other non-spherical geometries. Accordingly, the invention relates to methods of producing HPVLPs that are substantially spherical in geometry. The invention includes HPVLP preparations where at least about 10%, about 15%, about 20%, about 25%, about 50%, about 60%, about 65%, about 70%, about 80%, about 90%, about 95%, or about 99% of the HPVLPs in the preparation resemble the naturally-occurring JCV capsid (e.g., are in an icosahedral or substantially spherical configuration). In some embodiments, an HPVLP preparation contains at least 10%, 15%, 20%, 50%, 60%, 70%, 80%, 90%, 95%, or 99% of the HPVLPs in the preparation resemble the naturally-occurring JCV capsid. Such methods can include expressing viral proteins under conditions that result in such a preparation and/or isolating and purifying expressed viral proteins as described herein to produce such a preparation.

Methods of making HPVLP

HPVLPs can be made, for example, by transforming a baculovirus with a vector expressing a VP1 gene, such as a VP1 gene from a JC virus. The baculovirus is used to infect a cell culture, such as an insect cell culture (e.g., SF9 cells) or a mammalian cell culture, and the cells express the VP1 protein. HPVLPs are isolated by lysing the cells, and purifying the particles through a series of centrifugation and ultrafiltration steps. In general, the purification is performed using methods such as sucrose cushion sedimentation, isopycnic ultracentrifugation and extensive ultrafiltration or other methods known to those in the art. In certain embodiments, the purification will include twice centrifuging the particles through a sucrose cushion. In an alternative purification method, cells are lysed, and particles are isolated by a series of precipitation and concentration/diafiltration steps with a final ion-exchange step.

Purity can be assessed using any suitable techniques known in the art, for example, analytical ultracentrifugation, electron microscopy, PAGE analysis, mass spectrometry, protein concentration, or activity in an ELISA with control sera. Insufficiently purified VLPs result in a high background yielding falsely high JCV antibody levels or calculated exposure rates.

In some embodiments, the HPVLPs contain VP1 as the sole JC virus protein.

In some embodiments, the HPVLPs are heterogeneous particles, and therefore include VP1 protein, and at least one of the minor coat proteins of JC virus, e.g., VP2 or VP3. In another embodiment, the HPVLP includes VP1, VP2 and VP3 proteins. An HPVLP that includes VP1 and VP2 can be produced using methods known in the art, for example, by transforming a baculovirus with a nucleic acid including a VP1 and a VP2 gene, such as under the control of the same or different promoters. A cell culture is infected with the baculovirus, and the cells express VP1 and VP2, and HPVLPs form which include both types of proteins. In one embodiment, the VP1 and VP2 genes are on different DNA molecules, the DNA molecules are transformed into different baculoviruses and the baculoviruses are used to transfect cells in the same culture. The cells express the VP1 and VP2 proteins, and HPVLPs form which include both types of protein. In some cases, a heterogeneous HPVLP will include, e.g, one or two VP2 polypeptides for every five VP1 polypeptides. In general, an HPVLP will contain more VP1 polypeptides than VP2 polypeptides, as is the case in naturally-occurring JC virus.

An HPVLP that includes both VP1 and VP3 or both VP1 and VP2 molecules can be produced, for example, by transforming a baculovirus with a nucleic acid including a VP1 and a VP3 gene or a VP1 and VP2 gene, respectively, under the control of the same or different promoters. A cell culture is infected with the baculovirus, and the cells express VP1 and VP3 or VP1 and VP2, and HPVLPs form which include both types of proteins. In some embodiments, the VP1 and VP3 or VP1 and VP2 genes are on different DNA molecules, the DNA molecules are transformed into different baculoviruses, and the baculoviruses are used to transfect cells in the same culture. The cells express the VP1 and VP3 proteins or VP1 and VP2 genes, respectively, and HPVLPs form which include both types of protein. HPVLP particles can be isolated from such preparations using methods known in the art such as those used to isolate JCV capsids.

Typically, a VP1 pentamer that is in a heterogeneous HPVLP will include, e.g, five VP1 polypeptides and one VP3 polypeptide and/or one VP2 polypeptide, depending on whether a VP3 gene or VP2 gene was used to make the constructs. There will typically be more VP1 polypeptides than VP3 or VP2 polypeptides in an HPVLP. In some embodiments, the VP2 or VP3 is from a polyoma virus that is not a JC virus, e.g., a BK virus polypeptide.

An HPVLP that includes all three of VP1 and VP2 and VP3 molecules can be produced by transforming a baculovirus with a nucleic acid (e.g., a circular DNA, e.g., <5.5 kb) including a VP1, VP2 and VP3 gene, such as under the control of the same or different promoters. A cell culture, such as a mammalian cell culture, is infected with the baculovirus, and the cells express VP1, VP2 and VP3 proteins. HPVLPs consequently form which include all three types of proteins. In one embodiment, the VP1, and either or both of the VP2 and VP3 genes are on different DNA molecules, the DNA molecules are transformed into the same or different baculovirus, and the baculovirus are used to infect cells in the same or separate cultures. The cells express the VP1, VP2 and VP3 proteins, and HPVLPs form which include both types of protein. A heterogeneous HPVLP can include, e.g, five VP1 polypeptides and one each of VP2 and VP3 polypeptides, although the ratios may vary within a preparation. There will typically be more VP1 polypeptides than VP2 and VP3 polypeptides in an HPVLP.

In some embodiments, the HPVLP will be greater in size than a VP1 pentamer. By greater in size, it is meant that the mass of protein contained in an HPVLP particle is greater than a pentamer containing solely VP1.

In other embodiments, the method of preparing a solution of HPVLP can include removing from the solution particles (e.g., VP1 monomers or small VP1 containing particles) that are the size of a VP1 pentamer or smaller. Methods such as centrifugation and size-exclusion chromatography can be used to perform this purification step. In some embodiments, other methods known in the art, e.g., ion exchange chromatography, can be used in the preparation of HPVLPs that are larger than a VP1 pentamer. In general, an HPVLP preparation suitable for use in an assay will contain at least 20% HPVLPs, at least 25% HPVLPs, at least 40% HPVLPs, at least 60% HPVLPs, at least 65% HPVLPs, at least 70% HPVLPs, at least 80% HPVLPs, at least 85% HPVLPs, at least 90% HPVLPs, at least 95% HPVLPs, or at least 99% HPVPLs compared to non-HLVLP particles (e.g., by percent of pentamers compared to VP1 monomers and aggregates containing fewer than five VP1 molecules).

Cut point

The invention provides methods of analysis that employ "cut points" to reduce false negative and false positive rates. The cut points are established based on data from the HPVLP assays (e.g., to detect JCV antibodies in a biological sample), averaged, for example, between duplicate test samples and multiple replicates (for example, at least two, at least four, or at least eight replicates of control samples).

In one version of an assay according to the present invention, results from initial HPVLP screening assays, e.g., ELISA assays, will cause a test sample to be classified as having or not having JCV-specific antibodies, or, if the sample does not fall under one of these two classifications, then the sample will be subjected to a supplemental confirmation assay. For example, samples that produce a result in an HPVLP ELISA assay featured in the invention less than an established level (e.g., an $nOD_{450}<0.1$) will be classified as lacking JCV-specific antibodies, and samples that provide a result in the ELISA greater than an established level (e.g., an $nOD_{450}>0.25$) will be classified as positive for JCV-specific antibodies. Samples that do not clearly fall into one of these classifications (e.g., 0.1<OD450<0.25) can be tested in a confirmatory assay.

In one embodiment, the confirmatory assay requires a pre-incubation step, where the test sample is pre-incubated with buffer (or other suitable solution) control or with HPVLPs (in buffer or other suitable solution) to pre-adsorb JCV-specific antibodies prior to analysis in an HPVLP ELISA, as described in further detail below. After pre-incubation with HPVLP if the reaction in the primary assay decreases by less than 40% compared to buffer control, then the sample is interpreted to be negative for the presence of JCV-specific antibodies. If the results show a ≥40% reduction in reaction compared to buffer control in the primary assay after pre-incubation with HPVLP then the sample is interpreted to contain JCV specific antibodies. In some embodiments, only the confirmatory assay is performed.

An example of a method for selecting and verifying suitable cut points is provided in Example 4.

Substrate

Any suitable solid substrate can be used for the HPVLP assay format. In some embodiments, the substrate is a microtiter plate (e.g., a 96-well plate) a slide, a bead, or a column. The substrate can be suitable for chromogenic or chemiluminescent detection methods.

Assay

Assays are conducted by adding a biological sample to a substrate that has been coated with an HPVLP and detected using methods known in the art. In general, a solid base platform is used such as a microtiter plate (for example, a 96 well plate); although other formats known in the art can be used. In some embodiments, the biological sample is diluted prior to use in an assay.

In certain embodiments, the assay format is an enzyme-linked immunoassay (ELISA). Broadly, the method typically includes coating the substrate with capture antigen such as HPVLP, incubating sample containing binding antibodies directed to capture reagent, washing to remove non-specifically bound species, and detecting the bound immune complexes, e.g., by a chromogenic or chemiluminescent assay. Chromogenic substrates produce a colored end product, which can be detected and measured visually or with the use of a spectrophotometer. Chemiluminescent substrates produce light, which can be measured using a luminometer.

Coating a plate with HPVLP generally includes incubating the solid substrate (such as wells of a microtiter plate) with a solution of HPVLP at a suitable concentration (e.g., 1 µg/ml), either overnight or for a specified number of hours. The HPVLP can include VP1 as the only JCV viral component, or the HPVLP can be a heterologous particle, that contains at least one of VP2 or VP3 per particle or at least one each of VP2 and VP3 per particle. After coating with the HPVLP, the wells of the plate are washed. The substrate is then "coated" with a nonspecific protein that is antigenically neutral with regard to the samples to be tested. Suitable coating materials are known in the art and include bovine serum albumin (BSA), casein or solutions of milk powder.

The sample or reference is incubated on the prepared substrate under conditions effective to permit complex formation (HPVLP/JCV antibody), thus forming a bound complex. Detection of the bound complex is performed using a labeled antibody that can bind to human antibody. In general, the labeled antibody can detect human IgG or human IgG and IgM. In some cases, the assay can be performed using secondary or tertiary detection methods.

A reference sample can be of the same biological material (e.g., plasma, serum, urine, or CSF) isolated from an individual known to be infected with JC virus based on the presence of JCV DNA in urine of the individual (uropositive). A reference sample is used to establish the assay cut point such that the false negative rate of the assay is not greater than 1%-3%.

"Under conditions effective to permit complex formation" generally means conditions in which the reagents have been diluted to reduce background and provide readouts of results that lie within a specified range. Diluents can include, in non-limiting examples, solutions that include BSA, phosphate buffered saline (PBS), or PBS containing TWEEN®.

"Suitable" conditions also include conditions that are at a temperature and/or for a period of time sufficient to allow effective binding. Incubations are typically from about one to two hours or one to four hours, at temperatures of approximately 25° C. to 27° C., or may be overnight at about 4° C. However, those in the art will understand that other conditions may be suitable.

In general, one or more washes are conducted between the incubations of the assay. Appropriate wash solutions include diluent buffer (e.g., PBS or PBS/TWEEN®) or borate buffer.

In general, the detection of antibody bound to HPVLP is performed using methods well known in the art. In general, such methods are based on the detection of a label or marker, such as a radioactive, fluorescent, biological or enzymatic tag. U.S. patents concerning the use of such labels include, for example, U.S. Pat. Nos. 3,817,837; 3,850,752; 3,939,350; 3,996,345; 4,277,437; 4,275,149 and 4,366,241. In general, the detection of JCV antibody binding is detected using a secondary antibody that is labeled. In general, the secondary antibody is specific for detecting human IgG. Quantification is achieved by measuring the degree of color generated, e.g., using a visible spectra spectrophotometer.

Example 2 illustrates a method of performing the assay and those in the art will understand that suitable modifications can be made.

In one embodiment, the assay is performed in a medical office, such as by a healthcare provider, e.g., a doctor, a nurse or a technician, working in a facility where the biological sample is obtained from a patient. In another embodiment, the biological sample obtained from a patient is transported to another facility, e.g., to a third party facility, where the assay is performed. In this latter case, the results of the assay can be reported back to the healthcare provider, such as through a form, which can be submitted by mail or electronically (e.g., through facsimile or e-mail) or through an on-line database. In one embodiment, the results of the assay (including the screening assay and, optionally, a confirmatory assay) can be stored in a database and can be accessed by a healthcare provider, such as through the worldwide web.

Secondary Test

In some cases, for example, when the level of JCV antibody in a sample falls into a designated "equivocal zone" or "indeterminate zone," e.g., where it is determined that there is limited certainty regarding the presence or absence of JCV antibody, a secondary test (also referred to herein as a "confirmatory assay") of the sample is employed. For the secondary test, two aliquots of a biological sample are used. The first is prepared prior to use in the assay by preincubating the sample in the presence of assay buffer in solution for a period of time (e.g., for 30 minutes, one hour, or longer such as overnight at 4° C.). The second aliquot is prepared prior to use in the assay by preincubating the sample in the presence of HPVLP in solution for a period of time (e.g., for 30 minutes, or one hour or longer). The two aliquots are then used in the HPVLP assay as described herein, and the assignment of the sample to JCV antibody positive or antibody negative is made. If the assay results for the aliquot incubated with HPVLP in solution is the same as for the first aliquot incubated with buffer in the primary assay (i.e., approximately the same OD), then the sample is interpreted to be negative for the presence of JCV-specific antibodies. If the assay results are lower after pre-incubation (i.e., in the secondary assay), then the sample is interpreted to contain JCV specific antibodies.

An assay featured in the invention that utilizes a secondary test is also referred to herein as a "two-step test" or a "two-step assay."

Reporting of Assay Results

In some embodiments, the assay includes a read out that can be a level (e.g., OD) relative to a reference or a read out that is an evaluation of whether the sample is positive, negative, or indeterminate for the presence of JCV antibodies. In some embodiments, a kit is provided that includes at least HPVLP and optionally, other components for an assay. For example, the kit can include assay positive and negative controls, buffers and substrates (e.g., microtiter plates) for preparing the tools to perform the primary ELISA assay, and the secondary confirmation assay. The kit can include, e.g., solvents or buffers, controls, a stabilizer, a preservative, a secondary antibody, e.g., an anti-HRP antibody (IgG) and a detection reagent.

The HPVLP can be provided in any form, e.g., liquid, dried, semi-dried, or lyophilized form, or in a form for storage in a frozen condition. In some embodiments, prepared HPVLPs are pelleted and stored in a semi-solid form.

Typically, HPVLPs are provided in a form that is sterile. When HPVLP is provided in a liquid solution, the liquid solution generally is an aqueous solution, e.g., a sterile aqueous solution. When the HPVLP is provided as a dried form, reconstitution generally is accomplished by the addition of a suitable solvent. The solvent, e.g., sterile buffer, can optionally be provided in the kit.

The kit can include one or more containers for the composition containing HPVLPs in a concentration suitable for use in the assay or with instructions for dilution for use in the assay. In some embodiments, the kit contains separate containers, dividers or compartments for the HPVLP and assay components, and the informational material. For example, the HPVLPs can be contained in a bottle or vial, and the informational material can be contained in a plastic sleeve or packet. In other embodiments, the separate elements of the kit are contained within a single, undivided container. For example, an HPVLP composition is contained in a bottle or vial that has attached thereto the informational material in the form of a label. In some embodiments, the kit includes a plurality (e.g., a pack) of individual containers, each containing one or more unit forms (e.g., for use with one assay) of HPVLP. For example, the kit includes a plurality of ampoules, foil packets, or blister packs, each containing a single unit of HPVLP for use in a screening or confirmatory assay. The containers of the kits can be air tight and/or waterproof. The container can be labeled for use.

In one embodiment, the kit can include informational material for performing and interpreting the assay. In another embodiment, the kit can provide guidance as to where to report the results of the assay, e.g., to a treatment center or healthcare provider. The kit can include forms for reporting the results of an HPVLP assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with an immunomodulatory drug, depending on the results of the assay.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about HPVP assay and/or its use in the methods described herein. Of course, the informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a plasma, blood or serum sample, and evaluates the sample using an assay described herein, and determines that the sample contains JCV antibodies. The assay provider, e.g., a service provider or healthcare provider, can then conclude that the subject is at increased risk for PML. The assay provider can further determine that the subject is not a candidate to receive treatment with an immunomodulator, such as an anti-VLA therapy, such as natalizumab, or that the subject is a candidate to receive treatment with an immunomodulator, but the candidate will have enhanced monitoring as compared to a subject who is determined not to have JCV antibodies. For example, the candidate will be examined more frequently for the development of adverse symptoms, such as symptoms that may indicate the development of PML.

In one embodiment, the assay provider performs an assay described herein and determines that a subject does not have detectable JCV antibodies. The assay provider further determines that the subject is a candidate to receive treatment with an immunomodulator, such as natalizumab. In one embodiment, the assay provider informs a healthcare provider that the subject is a candidate for treatment with the immunomodulator, and the candidate is administered the immunomodulator.

The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

The invention is further illustrated by the following examples, which should not be construed as further limiting.

Examples

Example 1: Synthesis and Purification of Highly Purified VP1 Particles

HPVLPs consisting of JCV or BKV capsid protein VP1 were produced in SF9 insect cells transfected with a recombinant baculovirus. In the case of JCV VP1 containing particles, recombinant baculovirus was transformed with a nucleic acid expressing VP1 from the Mad-1 strain of JCV. The recombinant VLP was harvested prior to cell lysis and was purified by differential ultracentrifugation, detergent washing and ultrafiltration.

Briefly, baculovirus infected cells were harvested about three days post infection by centrifugation at 3000×G and stored frozen until purification of HPVLPs. Purification was performed using about 100 grams of frozen cell pellets. Thawed cells were lysed in 500 ml of PBS supplemented with 0.1 mM $CaCl_2$ (PBS-C). The cells were disrupted by passing the cell suspension twice through a Microfluidics Microfluidizer®. Cell debris was removed by pelleting at 8000 ×G for 15 minutes. The supernatant volume was adjusted to 720 ml with PBS-C and loaded onto 5 ml 40% sucrose cushions. HPVLPs were twice pelleted through the sucrose cushions in a SW28 rotor at 100,000×G for 5 hours. The HPVLP pellets were resuspended in PBS-$CaCl_2$) and then treated with 0.25% deoxycholate for 1 hour at 37° C. followed by the addition of 4 M NaCl supplemented with 0.1 mM $CaCl_2$) for 1 hour at 4° C. Precipitated material was removed by centrifugation at 8000×G for 15 minutes. The resulting supernatant was concentrated and buffer exchanged by ultrafiltration through a PELICON®-2 500,000 MWCO membrane (Millipore). The concentrated VLPs were applied to the center of a 25-40% step gradient of Optiprep™ (Sigma, St. Louis, Mo.) and banded at 190,000 g for 17 hours in a Type 50.2 rotor. VLP bands were collected and then concentrated and buffer exchanged in an AMICON® stirred cell (Millipore) with a 300,000 MWCO (molecular weight cut-off) membrane. The concentrated material was filtered through a 0.22 μPES (polyethersulfone)

filter and stored at 4° C. VLPs prepared in this way are termed HPVLPs herein. VLP quality is generally determined by gel electrophoresis and electron microscopy.

To denature the VLPs for protein determination, EDTA, DTT and SDS were added to final concentrations of 2 mM, 2 mM and 2% respectively. The concentration of the fully denatured protein was determined by using the PIERCE' BCA (bicinchoninic acid) assay.

For analysis by gel electrophoresis, a sufficient volume to give 2 µg to 5 µg of total protein was loaded on precast 4% to 20% polyacrylamide gels (NOVEX, San Diego, Calif.) by using a NuPAGE® morpholineethanesulfonic acid-SDS buffer system (Invitrogen, Carlsbad, Calif.). The gels were electrophoresed at a constant current of 70 mA/gel to 80 mA/gel for 30 minutes. Protein bands were fixed with 50% methanol and 10% acetic acid in distilled water and visualized with a commercial colloidal Coomassie blue reagent (Invitrogen) according to the recommendations of the manufacturer.

VLPs were evaluated using electron microscopy. VLP samples were placed on carbon grids, briefly washed in water and negatively stained with uranyl acetate and allowed to dry. The grids were viewed and imaged on a Tecnai™ G2 Spirit BioTWIN TEM.

An alternative JCV VP1-VLP purification method is presented below, at Example 7.

Example 2: HPVLP Antibody Assay

A sensitive assay for anti-JCV antibodies was developed using the HPVLPs described herein and is referred to herein in its various embodiments as an HPVLP assay. In an example of the assay, 96 well microtiter plates were prepared by adding a solution containing HPVLP at a concentration of 1 µg/ml and incubating the plate overnight at 4° C. The wells were rinsed with diluent buffer and then blocked for one hour at room temperature with Casein Blocking Buffer and rinsed with diluent buffer. The assay controls and serum or plasma samples were diluted 1:200 in assay diluent. The diluted samples and controls were added to wells and incubated for one hour at room temperature and washed with diluent buffer. Detection was performed using donkey anti-human-HRP antibody (IgG), which was added to the wells and incubated at room temperature for one hour. Plates were then washed and TMB (3,3',5,5'-tetramethylbenzidine) buffer (Chromagen, Inc., San Diego, Calif.) was added. After a development for a time suitable to permit color to develop (about 20 minutes), the reaction was stopped with 1 N $H_2SO_4$, and the absorbance at 450 nm was read. Levels of anti-JCV antibody in the samples were expressed as OD units.

The assay was interpreted as described below using the OD units to determine levels.

In secondary testing, if unknown samples produced greater than 40% competitive inhibition of binding with HPVLP in solution, the sample was considered JCV+(JCV positive), with <40% inhibition being scored as JCV−(JCV negative).

Initially, samples with OD values greater than the cut point OD (mean Negative Control OD×1.23) were defined as positive for the presence of JCV antibodies, whereas samples with OD values equal to or less than the cut point OD were defined as negative.

Controls used in the assay were selected based on target OD and specificity (as determined in the secondary confirmation assay for specificity (described infra) and included Positive Control 1, which was pooled donor sera with high reactivity in the assay defined as having target OD value of about 1.0 and for specificity, competed with JCV >80%; Positive Control 2, which contained pooled donor sera with lower reactivity in assay defined as having a target OD value of about 0.25 in the assay; and for specificity competed with JCV >80%; and Negative Control, which was pooled donor sera with reactivity similar to buffer control in assay having a target OD value of approximately 0.07 (note that the assay buffer has an O.D. value of approximately 0.045).

In some cases, a titration assay was conducted in which positive samples were tested at multiple dilutions, and the highest dilution giving an OD value greater than the cut point OD was defined as the JCV IgG titer.

The assays have been validated from the perspective of specificity, precision, matrix interference, robustness, and reagent stability.

Example 3: Secondary Confirmation Assay

In some cases, a secondary confirmation assay (secondary assay) was carried out in addition to the test described supra. In the confirmation assay, samples (plasma or serum) were incubated with HPVLP (final VLP concentration=1 µg/mL; final sample dilution=1:200) for one hour at room temperature prior to use in the assay. Control samples were incubated in assay buffer, and not in the presence of HPVLP. The assay was then conducted as described above. A percent $nOD_{450}$ inhibition was calculated as: % inhibition=100 ×[1- (average $nOD_{450}$) (JCV MAD-1 VLP pre-incubated samples) ÷(average $nOD_{450}$) (buffer incubated samples)].

If the assay results were the same after pre-incubation with buffer as in the primary assay (i.e., approximately the same O.D.), then the sample was interpreted to be negative for the presence of JCV-specific antibodies. If the assay results were lower after pre-incubation with HPVLPs (i.e., in the secondary assay), then the sample was interpreted to contain JCV-specific antibodies.

Example 4: Screening/Confirmation Assay Cut Point Algorithm

The serological test (JCV antibody test) was configured as a two-step assay: a screening ELISA and a supplemental confirmation ELISA (secondary assay).

For comparison of results between assay plates, assay runs, and analysts, sample results were normalized to the optical density ($OD_{450}$) value of the positive control on the plate and reported as normalized $OD_{450}$ as described below.

To implement the utility of the HPVP assay, cut points were derived using a Weibull three component mixture-distribution model. In these determinations, the following definitions were used:

$$\text{Screening assay normalized } OD \ (nOD) = \frac{avg(\text{sample\_OD\_duplicates})}{avg(PC1\_OD\_\text{replicates})};$$

For example:
Average (sample_OD_duplicates)=0.60
Average (Positive Control 1 OD_replicates)=1.20
Normalized OD=0.60/1.20=0.50.
For the Confirmation Assay Confirmation assay % inhibition=

$$100\% \times \left(1 - \frac{\text{competition\_sample\_OD}}{\text{noncompetition\_sample\_OD}}\right)$$

In the supplemental confirmation ELISA, soluble HPVLP was used to pre-adsorb high affinity antibodies against JCV in samples prior to evaluation of the samples in the screening ELISA. Results were calculated as percent inhibition to determine decreases in reactivity in the screening ELISA after the samples were pre-adsorbed with HPVLP [% inhibition=100 ×[1- (average $nOD_{450}$ HPVLP pre-incubated samples) ÷(average $nOD_{450}$ buffer incubated samples)].

False positive and false negative rates were defined as follows. The false negative rate is the proportion of true JC virus positive samples that are determined to be antibody negative by the assay. The sero-positive rate is the proportion of samples determined to be sero-positive (i.e., have JCV antibodies as determined using the anti-JCV screening/confirmation cut point algorithm).

Data were analyzed using SAS v9. Data not demonstrating a normal distribution were analyzed by the Mann-Whitney U test. Categorical data were analyzed using Pearson's $\chi 2$ test or Fisher's exact test depending on the sample size. Pearson's correlation coefficient was used to asses the relationship between $nOD_{450}$ and urinary JCV DNA levels. All tests were two-sided at an alpha level of 0.05. Confidence limits for the seroprevalence and false-negative rates were obtained by the bootstrap percentile method (6) using 10,000 bootstraps.

Example 4(a): Serological Reactivity to JCV

A study was conducted to establish an assay to detect anti-JCV antibodies in MS patients and to conduct a preliminary evaluation of the potential clinical utility of the assay for PML risk stratification. To characterize antibody responses against infectious agents in humans, it was critical to have reference sera from both infected and non-infected individuals. While the asymptomatic nature of JCV infection makes it impossible to identify "true" negative individuals, Applicants were able to identify a population of "true" positive individuals by measuring JCV DNA in the urine of "uropositive" individuals.

Urinary JCV DNA levels (collected in the STRATA (natalizumab reinitiation of dosing) clinical trial protocol) were determined by a quantitative real-time polymerase chain reaction (q-PCR) assay (ViraCor Laboratories, Lee's Summit, MO) with a limit of quantitation of 500 copies/mL and a limit of detection of 50 copies/mL.

The anti-JCV antibody status of 831 MS patient serum samples, which included samples from 204 JCV uropositive patients, was initially evaluated for anti-JCV antibodies in a screening ELISA to determine the distribution of serological responses. The assay results by urinary DNA status showed the presence of two overlapping yet distinct populations of JCV IgG reactivity (FIG. 1). The median level of reactivity for JCV DNA uropositive MS patients ($nOD_{450}$=0.895) was significantly higher than for JCV DNA uronegative MS patients ($nOD_{450}$=0.131; p<0.001), and no uropositive patient showed assay reactivity below a $nOD_{450}$ of 0.10. Therefore, a lower assay cut point was established at $nOD_{450}$ 0.10, wherein the empirical false-negative rate in the negative zone was 0%.

Many patients with no detectable JCV DNA in the urine (uronegatives) had serological reactivity similar to that of uropositive patients. These results are consistent with the assumption that a urine JCV DNA test is likely to fail to detect all JCV infected individuals.

Example 4(b): Urinary JCV DNA Load and Serological Activity

Figure 2:
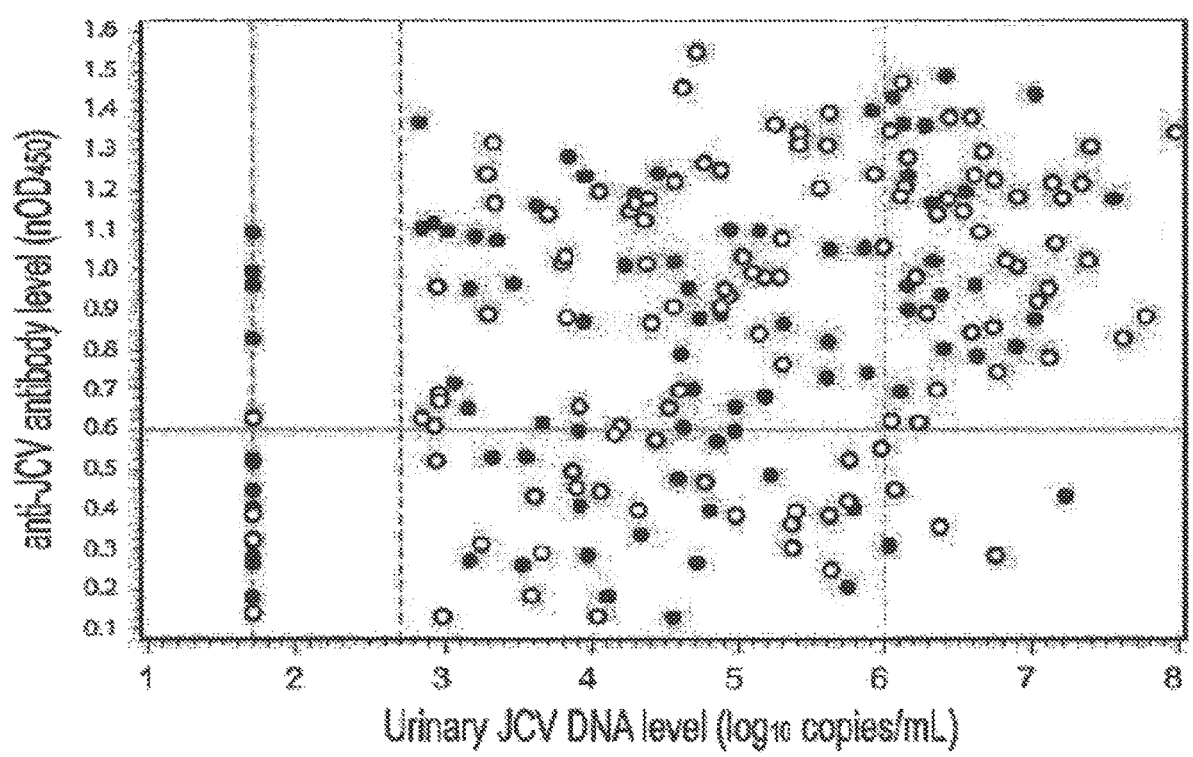
FIG. 2 is a graph depicting anti-JCV antibody levels as measured by ELISA against urinary JCV DNA level as measured by qPCR (n=204). Open circles represent urine and serum samples collected at matched STRATA time points. Closed circles represent samples collected at different time points. For 17 samples with DNA test results below the level of quantitation (<500 copies/mL) the level was set to the detection limit.

To address the potential concern that JCV infected patients with low levels of viral replication may have low serum antibody levels that are not detected in the serological assay (potential false negatives) the correlation between viral levels and antibody reactivity were examined. FIG. 2 shows data from the 204 JCV DNA uropositive STRATA patients, and illustrates that there is no detectable relationship between urinary JCV DNA levels and anti-JCV antibody levels in samples with $nOD_{450}$ below 0.60 (Pearson's correlation coefficient=0.048, p=0.751). This result holds true even if the urine and serum were collected at the same STRATA study time point (Pearson's correlation coefficient=0.002, p=0.993). At $nOD_{450}$>0.60, a stronger correlation was observed with a higher proportion of serum samples from individuals with high JCV DNA copies/mL exhibiting higher $nOD_{450}$ values, consistent with literature reports (e.g., Egli et al., J. Infect. Dis. 199:837-846, 2009). These data suggest that seronegative results are likely due to an absence of JCV infection, rather than to very low viral levels.

Example 4(c): Assessment of BKV-JCV Cross Reactivity

Assignment of a single conservative cut-point that controls the false-negative rate at 0% is unlikely to exclude detection of antibodies that cross-react to other common polyoma viruses (false positives), such as anti-BKV antibodies, which share high identity to JCV in the VP1 capsid protein. Additionally, such antibody cross-reactivity may occur through exposure of conserved viral epitopes when the HPVLP is directly coated onto the ELISA plate. Because dual infections with BKV and JCV may occur in humans and it is not possible to reliably identify patients who have been infected with BKV and not JCV, the issue of cross-reactivity was examined in rabbits, a species in which natural infection with either BKV or JCV cannot occur.

Figure 3:
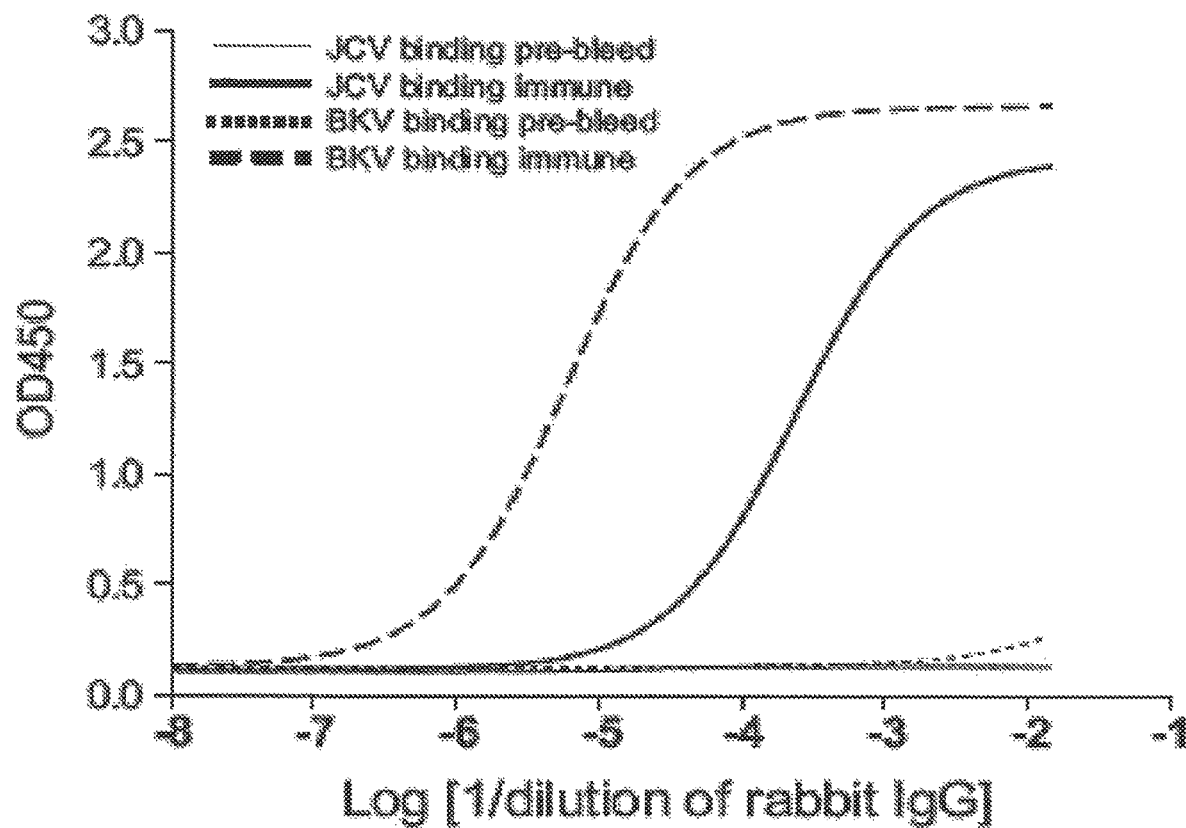
FIG. 3 is a graph depicting BKV-JCV cross-reactivity data from one rabbit immunized with BKV. Antisera from the BKV-immunized rabbit bound BKV VLPs with high affinity (EC50=1:100,000) and cross-reacted with JCV VLPs (EC50=1:5,000).

Rabbits were immunized with BKV by subcutaneous injection of proteins in phosphate-buffered saline without adjuvant, followed by three booster injections over a three month period. Serum samples were assayed for direct binding to JCV or BKV by ELISA. Antisera from BKV-immunized rabbits bound BKV VLPs with high affinity (EC50=1:100,000) and cross-reacted with HPVLPs with lower affinity (EC50=1:5,000). Pre-immune sera showed no reactivity. Representative data from one rabbit are shown in FIG. 3.

Because BKV antibodies cross-reacted with JCV, thus producing a false positive signal in the anti-JCV assay (FIG. 3), low level reactivity against JCV in humans could represent low affinity anti-BKV antibodies that cross-react with JCV to produce false-positive signals.

Example 4(d): Measuring JCV-Specific Antibody Response (Supplemental Confirmation ELISA)

Figure 4A:
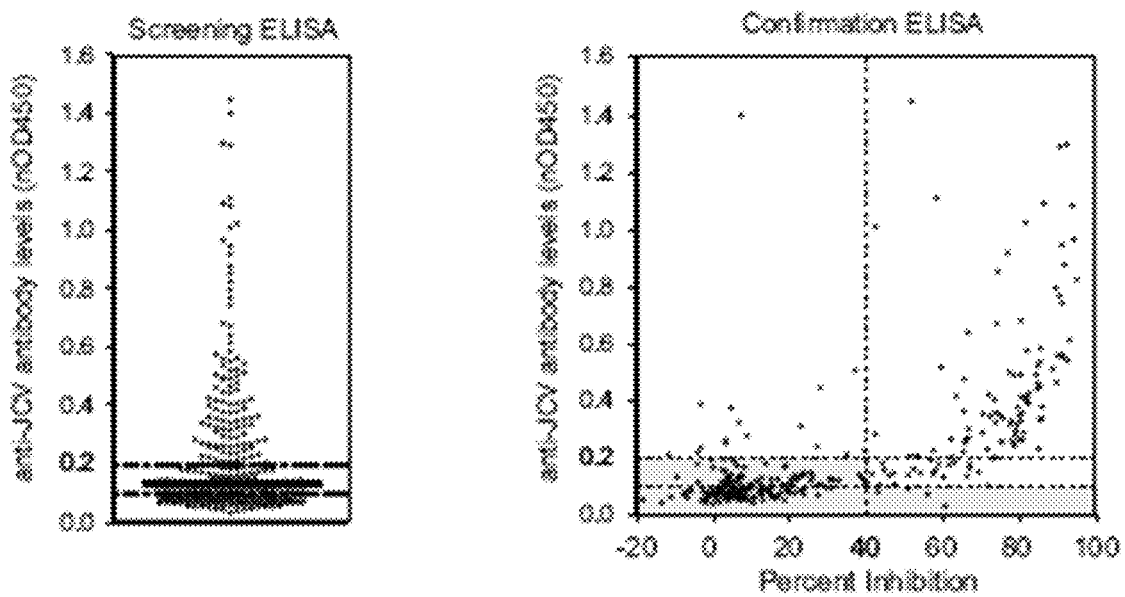
FIGS. 4A and 4B depict the anti-JCV assay reactivity of serum samples from uronegative (n=311) (FIG. 4A) and uropositive (n=204) (FIG. 4B) patients in the screening and confirmation ELISAs. Distribution of serological reactivity of the samples in the screening ELISA are shown, with lower ($nOD_{450}$=0.10) and upper ($nOD_{450}$=0.25) cut points highlighted (left panels). In the supplemental confirmation ELISA (right panels), a 40% inhibition cut point is highlighted (vertical line) with shaded regions denoting samples that did not confirm to have anti-JCV specific antibodies ($nOD_{450} \leq 0.25$ and percent inhibition $\leq 40\%$).
Figure 4B:
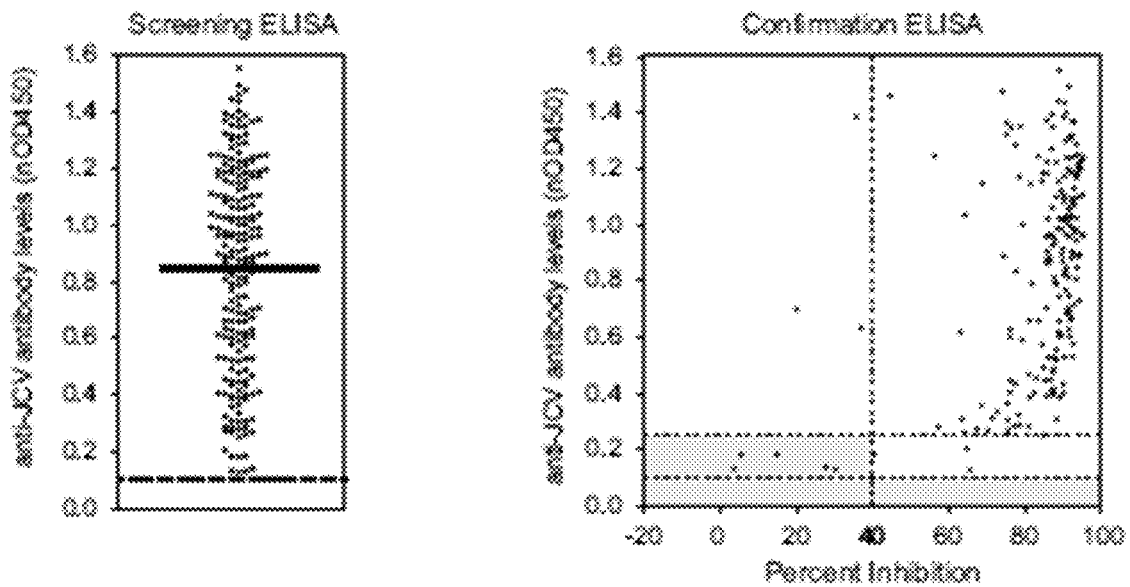

To distinguish patients with JCV-specific antibodies from those with potentially low affinity, cross reactive antibodies, a competition ELISA was developed using soluble HPVLP (secondary assay). JCV-specific higher affinity antibodies were expected to be more effectively competed by the soluble antigen, whereas lower affinity antibodies may detach from the complexes formed with the JCV antigen in solution and bind to the JCV VLP coated on the ELISA plate. A subset of 515 serum samples from uropositive (n=204) and uronegative (n=311) patients was systematically and non-proportionally sampled for evaluation in the ELISA after pre-adsorption with either soluble JCV VLP or assay buffer. In FIGS. 4A and 4B, the reactivity of serum samples from uronegative or uropositive patients in the screening and confirmation assays are shown side by side. Samples with strong JCV reactivity were highly inhibited by pre-adsorption of antibodies with soluble JCV, while samples with low levels of JCV antibodies showed differential competition. The antibody responses in most uropositive patients were strongly competed (FIG. 4B). These results support the idea that a significant proportion of the low serum reactivity to JCV may be due to cross-reactivity of antibodies not specific to JCV.

Figure 5A:
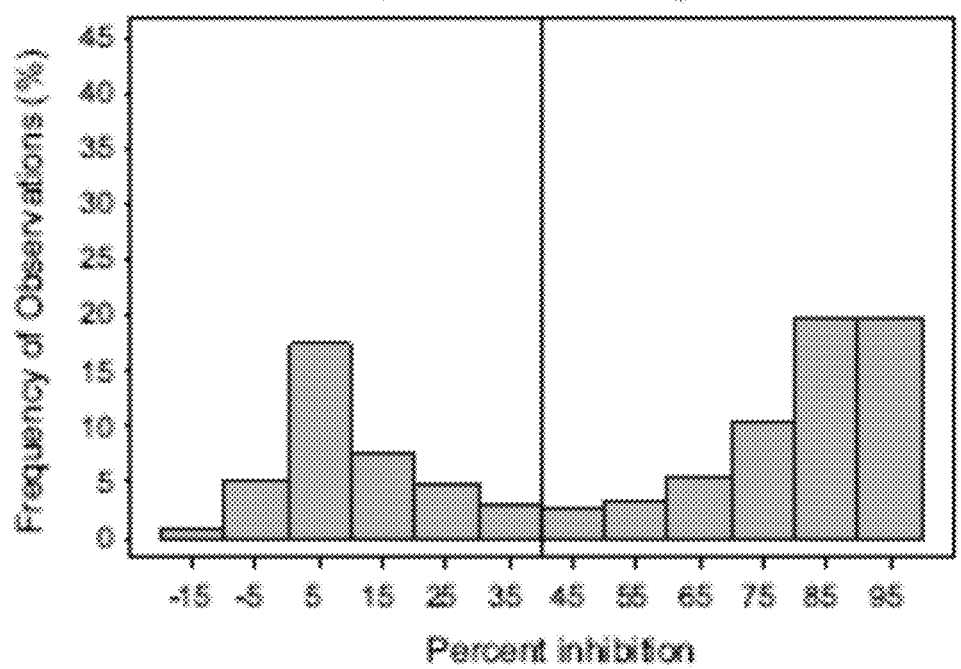
FIGS. 5A and 5B are histograms depicting the frequency of observations within each 10% inhibition range for all patients (n=515) (FIG. 5A) and uropositive patients (n=204) (FIG. 5B). The distribution consisted of two clearly defined peaks, most optimally separated at 40% inhibition. A 40% inhibition level corresponded to approximately the lower fifth percentile of the response distribution of uropositive samples.
Figure 5B:
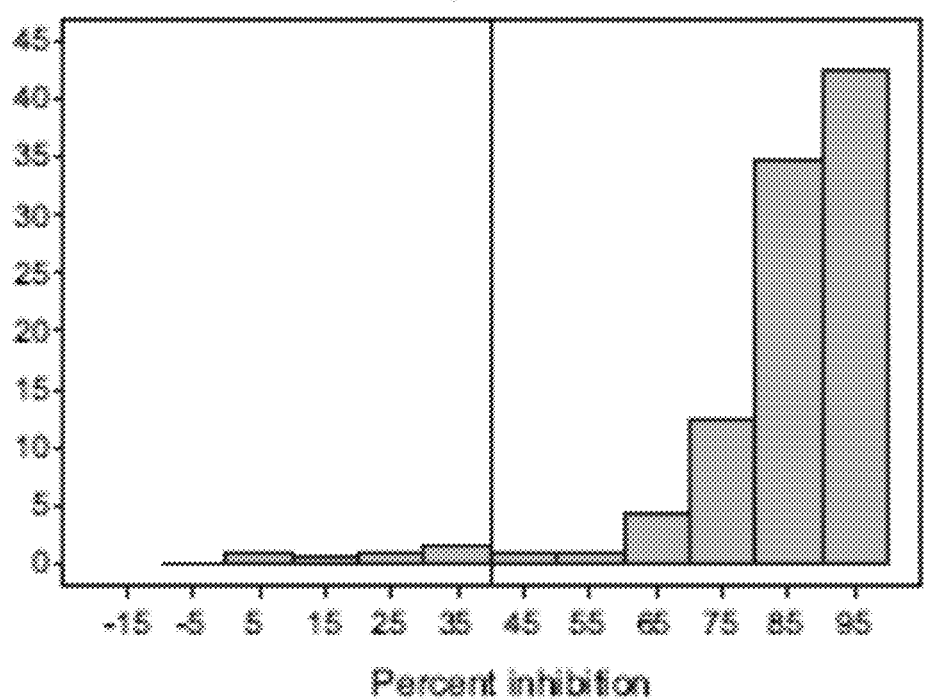

The distribution of the serum responses in the confirmation ELISA consisted of two defined peaks, most optimally separated at 40% inhibition (FIG. 5A) corresponding approximately to the lower 5th percentile of the response distribution of uropositive samples (FIG. 5B). Therefore, the 40% inhibition level was selected as the cut point for the confirmation ELISA.

Example 4(e): Finalized Two-Step Anti-JCV Serological Assay

By combining the screening and confirmation assays, the chance of detecting samples with "true" JCV-specific antibodies is greatly enhanced. In the final analysis, samples with $nOD_{450}$ values <0.10 in the screening ELISA are considered negative for JCV antibodies, and those with $nOD_{450}$ values >0.25 in the screening ELISA are considered positive for JCV antibodies. Samples with reactivity between nOD values 0.10 to 0.25 were further tested in the confirmation ELISA. In the confirmation ELISA, all samples exhibiting >40% inhibition are classified as positive (FIG. 4). At $nOD_{450}$ values >0.25 the probability of observing >40% inhibition was approximately 95%.

Example 4(f): JCV Seropositivity in the STRATA Cohort and False-Negative Rate Based on the above algorithm, the seroprevalence rate in STRATA population was estimated as 53.6% with bootstrap determined 95% confidence limits ranging from 49.9% to 57.3% [0.536=0.451 (probability of the screening ELISA $nOD_{450}$>0.25)+0.085 (probability of screening ELISA $nOD_{450}$ falling between 0.10 and 0.25, and the supplemental confirmation ELISA %-inhibition >40%)]. This seroprevalence calculation assumed confirmation of anti-JCV antibodies in equal proportions of samples from uropositive and uronegative subjects in the nOD region between 0.10 and 0.25. (percent inhibition >40%); this assumption was supported by a 2-sided Fisher's exact test with a p-value of 0.702.

Of the 204 uropositive patients, five had $nOD_{450}$ between 0.10 and 0.25 and did not confirm as having anti-JCV specific antibodies (percent inhibition ≤40%; FIG. 4B).

Example 5: Assay Validation

Assay validation was performed by Focus Diagnostics, Inc. (Cypress, CA), where performance parameters including inter- and intra-assay precision, specificity, sensitivity and stability of assay reagents and controls were demonstrated. Assay performance parameters including inter- and intra-assay precision, specificity, sensitivity and stability of assay reagents and controls was demonstrated. Precision parameters were evaluated by three independent analysts in both plasma and serum on four different days using independent preparations of assay controls. For demonstration of assay specificity, ten individual serum and plasma samples from healthy volunteers or MS patients (TYSABRI® (natalizumab) naïve) were pre-incubated with either assay buffer or a defined concentration of HPVLP or BKV VLP in solution. Robustness was evaluated by varying the upper and lower limits of incubation times for sample, conjugate, and substrate addition steps and different lots of HPVLP coating reagent were evaluated to demonstrate consistent assay control performance. Matrix interference was evaluated by determining percent recovery in samples spiked with pre-defined concentrations of anti-JCV antibodies and by spiking samples containing JCV-specific antibodies with varying concentrations of irrelevant human monoclonal antibodies.

Example 6: Determination of JCV Antibody Status in PML Patients

Plasma and serum samples (single time-points randomly selected from serial collections) were obtained from a total of 831 patients from the Safety of TYSABRI® Re-dosing And Treatment (STRATA) study. STRATA is an open-label, single-arm, multinational study (North America, Europe, Australia, and New Zealand) in which all patients receive natalizumab 300 mg by intravenous infusion every 4 weeks for 48 weeks. Urine samples collected according to the STRATA protocol were analyzed for the presence of JCV DNA.

Figure 6A:
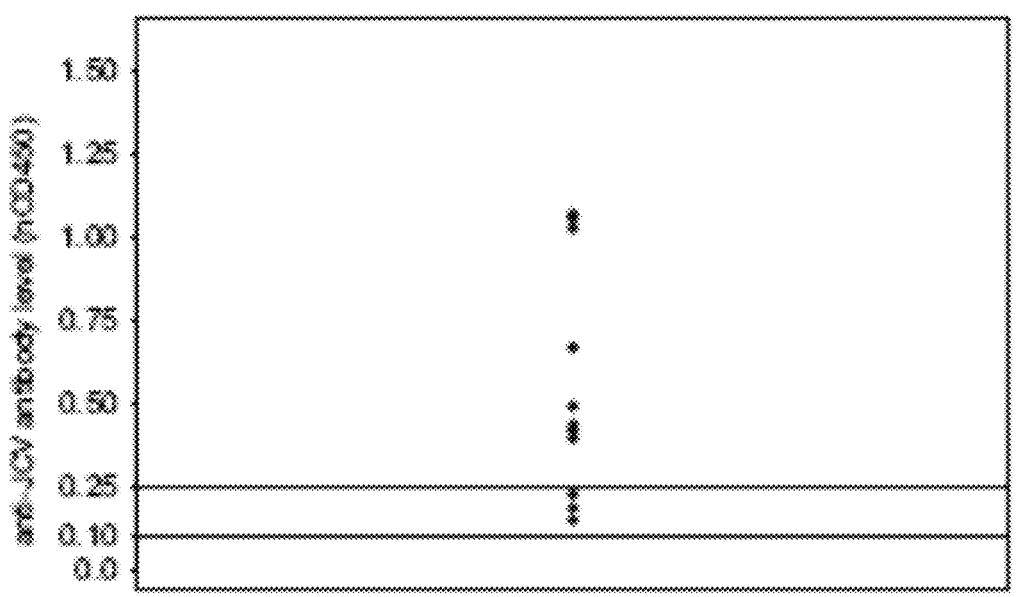
FIGS. 6A and 6B are plots of $nOD_{450}$ values from the screening ELISA (FIG. 6A) versus percent inhibition values from the confirmation ELISA (FIG. 5B) for the 11 pre-PML samples. Horizontal lines represent $nOD_{450}$ values of 0.10 and 0.25, the vertical line represents percent inhibition of 40%.
Figure 6B:
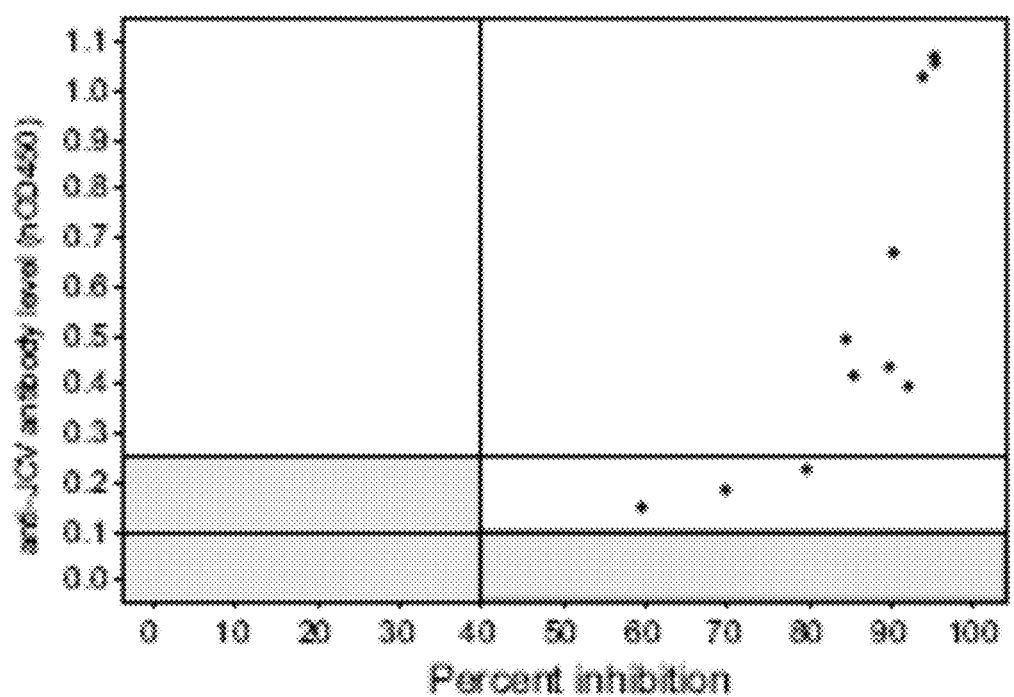

From the marketing approval of TYSABRI® in June 2006 to Feb. 9, 2010, there were 35 reported cases of PML on natalizumab treatment. In addition, there were three PML cases in the pre-approval clinical trials of natalizumab (10, 13, 25). Stored samples were obtained from as many PML cases as possible from time points prior to PML diagnosis (pre-PML). Plasma or serum samples were only available from 11 natalizumab-treated PML patients (10 MS patients and 1 Crohn's patient: Table 1). Serum samples were tested that were obtained one to three years prior to PML diagnosis. Nearly all of these samples had been collected from patients participating in registries or clinical studies and were stored at -70° C. until analysis. Notably, anti-JCV antibodies were detected in all 11 patients (100%) via the combination of the serological status screening ELISA and the supplemental confirmation ELISA (FIGS. 6A and 6B) described above. Using a one-sample Fisher's exact test, this result was significantly different from the expected proportion (53.6%) with a p-value of 0.002.

These data indicate that the assay of the present invention can be used to determine the presence or absence of JCV antibody in subjects as part of an overall evaluation of risk for contracting PML.

TABLE 1

Samples from 11 natalizumab-treated PML patients who had available blood samples prior to diagnosis.

| Subject | Source | Geography | PML Diagnosis (date) | Natalizumab Exposure No. of doses or months | Final dose | Immunosuppressant Use Type | Duration |
|---|---|---|---|---|---|---|---|
| 1 | Clinical Study* | Belgium | March 2005 | 5 doses | June 2003 | Infliximab Azathioprine | 32 months 73 months |

TABLE 1-continued

Samples from 11 natalizumab-treated PML patients who had available blood samples prior to diagnosis.

| Subject | Source | Geography | PML Diagnosis (date) | Natalizumab Exposure No. of doses or months | Natalizumab Exposure Final dose | Immunosuppressant Use Type | Immunosuppressant Use Duration |
|---|---|---|---|---|---|---|---|
| 2 | Clinical Study (SENTINEL) | United States | Febuary 2005 | 28 doses | December 2004 | None | |
| 3 | Clinical Study (SENTINEL) | United States | Febuary 2005 | 37 doses | January 2005 | None | |
| 4 | Post-Marketing | Sweden | July 2008 | 17 months | June 2008 | None | |
| 5 | Clinical Study (STRATA) | Germany | June 2009 | 34 doses | April 2009 | Mitoxantrone | 11 months |
| 6 | Clinical Study (STRATA) | France | June 2009 | 35 doses | May 2009 | Mitoxantrone | 10 months |
| 7 | Post-Marketing | Sweden | June 2009 | 29 months | June 2009 | None | |
| 8 | Post-Marketing | Switzerland | August 2009 | 28 doses/ 25 months | June 2009 | Mitoxantrone Azathioprine | 18 months 21 months |
| 9 | Post-Marketing | Switzerland | October 2009 | 36 months | September 2009 | Mitoxantrone | 4 years |
| 10 | Clinical Study (STRATA) | Czech Republic | October 2009 | 44 doses | September 2009 | Azathioprine | 3 months |
| 11 | Post-Marketing | United States | October 2009 | 33 doses | September 2009 | Methotrexate | Unknown |

*Crohn's Disease;
SENTINEL = Safety and Efficacy of Natalizumab in Combination with Interferon Beta-1a in Patients with Relapsing Remitting Multiple Sclerosis;
STRATA = Safety of TYSABRI Re-dosing and Treatment;
qd = 4 × day; qwk = 1 × week
SENTINEL = Safety and Efficacy of Natalizumab in Combination with Interferon Beta-1a in Patients with Relapsing Remitting Multiple Sclerosis;
STRATA = Safety of TYSABRI ® Re-dosing and Treatment;
ROW = Rest of World;
qd = 4 × day; qwk = 1 × week;
*Both prior and concurrent treatment with natalizumab Longitudinal data from other subjects taking an immunomodulator were also evaluated (i.e., multiple samples collected at different times from a single individual). The longitudinal data indicated that, unlike testing intermittent urinary DNA shedding, the HPVLP assay can reliably be used to evaluate anti-JCV antibody status, and that JCV antibody status remains relatively stable (in the absence of de novo infection).

Example 7: Alternate JCV VP1-VLP Purification Method

This method is an example of an alternative to the density-gradient/ultracentrifugation method described above for the purification of JCV VP1-VLP's from insect cells. The general steps in the protocol are lysis, BENZONASE® treatment, deoxycholate precipitation, ammonium sulfate precipitation and concentration/diafiltration, with a final ion-exchange step using TMAE fractogel.

Sf9 cells infected with JCV-VP1 baculovirus were lysed in PBS, 0.1 mM $CaCl_2$) by passing twice through a microfluidizer cell disrupter at 5,000 psi. Cell debris was removed by low speed centrifugation and the supernatant treated with 40 units/ml BENZONASE® (EMD Biosciences 71206-3) for 1 hour at room temperature. For the deoxycholate precipitation step, one tenth volume 2.5% deoxycholate was added to the lysate (0.25% final deoxycholate), and the lysate was incubated at 37° C. for 1 hour with gentle stirring. An equal volume of 4 M NaCl, 0.1 mM NaCl was added to the lysate and the lysate was incubated on ice for 1 hour. Precipitate was removed by low speed centrifugation. The supernatant was then precipitated with 40% ammonium sulfate to remove contaminating proteins. The final 40% was achieved by using 232 g solid ammonium sulfate per liter of solution. While mixing the solution gently at 4° C., ammonium sulfate was added one fifth at a time, allowing each addition to dissolve for 10 to15 minutes before adding the next fraction. The solution was stirred gently overnight at 4° C. The ammonium sulfate precipitate was removed by low speed centrifugation and the VP1-containing supernatant was filtered using a 0.45 μm filter and carried on to the next step. The solution was concentrated 5 to 10 fold using a 100 kDa NMWL TFF membrane (PELICON®-2 Mini UF Mod Biomax-100 C 0.1 $m^2$, P2B100001) and exchanged into assembly buffer (25 mM tris, 150 mM NaCl, 1 mM $CaCl_2$), pH 7.5) by diluting 5 fold and concentrating back to the starting volume twice. The solution was stored at 4° C. for >/=36 hours. The solution was then diafiltered using a 500 kDa NMWL TFF membrane (PELICON®-2 Mini UF Mod Biomax-500 V, Millipore part #P2B500V01) using 40 volumes TMA chromatography buffer (25 mM tris, 150 mM NaCl, 0.1 mM $CaCl_2$), pH 8.0). For the chromatography, approximately 1 ml resin is required per 2 g starting cell mass. The protein was loaded onto the appropriately sized TMAE column (Fractogel® EMD TMAE HiCap (M) EMD Biosciences cat. 1.10316) and washed with 3 column volumes chromatography buffer. The VLPs were eluted with 25 mM tris, 600 mM NaCl, 0.1 mM $CaCl_2$), pH 8.0. VP1 purity was assessed by SDS-PAGE and mass spectrometry, presence of VLPs was confirmed by electron microscopy, and the percentage of total protein in the form of VLPs was determined by sedimentation velocity analytical ultracentrifugation. This method resulted in HPVLP preparations of about 80% HPVLPs.

OTHER EMBODIMENTS

A number of embodiments of the invention have been described. Nevertheless, it will be understood that various modifications may be made without departing from the spirit and scope of the invention. Accordingly, other embodiments are within the scope of the following claims. PML diagnosis (pre-PML). Plasma or serum samples were only available from 11 natalizumab-treated PML patients (10 MS patients and 1 Crohn's patient: Table 1). Serum samples were tested that were obtained one to three years prior to PML diagnosis. Nearly, all of these samples had been collected from patients participating in registries or clinical studies and were stored at −70° C. until analysis. Notably, anti-JCV antibodies were detected in all 11 patients (100%) via the combination of the serological status screening ELISA and the supplemental confirmation (FIGS. 6A and 6B) described above. Using a one-sample Fisher's exact test, this result was significantly different from the expected proportion (53.6%) with a p-value of 0.002.

These data indicate that the assay of the present invention can be used to determine the presence or absence of JCV antibody in subjects as part of an overall evaluation of risk for contracting PML.

What is claimed is:

1. A reaction mixture comprising soluble JC Virus (JCV) virus-like particles (VLP), a sample of serum or plasma from a subject, and immobilized JCV VLP, wherein the immobilized JCV VLP has been coated with a blocking agent.

2. The reaction mixture of claim 1, wherein the soluble JCV VLP are highly purified virus like particles (HPVLP).

3. The reaction mixture of claim 2, wherein at least 20% of the HPVLPs comprise more than five VP1 polypeptides in an HPVLP.

4. The reaction mixture of claim 2, wherein at least 70% of the HPVLPs comprise more than five VP1 polypeptides in an HPVLP.

5. The reaction mixture of claim 2, wherein an HPVLP consists essentially of VP1 polypeptides.

6. The reaction mixture of claim 2, wherein an HPVLP further comprises at least one of a VP2, or a VP3.

7. The reaction mixture of claim 2, wherein the VP1 in the HPVLP is a recombinant VP1.

8. The reaction mixture of claim 2, wherein at least one VP1 in the HPVLP is a mutant VP1.

9. The reaction mixture of claim 1, wherein the immobilized JCV VLP are HPVLP.

10. The reaction mixture of claim 9, wherein wherein at least 20% of the HPVLPs comprise more than five VP1 polypeptides in an HPVLP.

11. The reaction mixture of claim 9, wherein at least 70% of the HPVLPs comprise more than five VP1 polypeptides in an HPVLP.

12. The reaction mixture of claim 9, wherein an HPVLP consists essentially of VP1 polypeptides.

13. The reaction mixture of claim 9, wherein an HPVLP further comprises at least one of a VP2, or a VP3.

14. The reaction mixture of claim 9, wherein the VP1 in the HPVLP is a recombinant VP1.

15. The reaction mixture of claim 9, wherein at least one VP1 in the HPVLP is a mutant VP1.

16. The reaction mixture of claim 1, wherein the sample is from a subject prescribed an immunomodulator, a subject considering taking an immunomodulator, or a subject suspected of having Progressive Multifocal Leukoencephalopathy (PML).

17. The reaction mixture of claim 1, wherein the blocking agent is a nonspecific protein that is antigenically neutral.

18. The reaction mixture of claim 17, wherein the blocking agent is selected from bovine serum albumin (BSA), casein, or a solution of milk powder.

19. The reaction mixture of claim 1, wherein the reaction mixture comprises anti-JCV serum antibodies bound to the soluble JCV VLP.

20. The reaction mixture of claim 19, wherein soluble JCV VLP and anti-JCV serum antibodies in the reaction mixture comprise a pre-formed complex.

21. A method comprising:
   (a) forming a reaction mixture comprising soluble JC Virus (JCV) VLP and an aliquot of a sample of serum or plasma from a subject, thereby performing a pre-treatment reaction mixture; and
   (b) incubating said reaction mixture of (a) under conditions suitable for the soluble JCV-VLP to bind anti-JCV antibodies in the reaction mixture, if present, thereby performing a pre-treatment step.

22. The method of claim 21, wherein the method further comprises:
   (c) after the pre-treatment, contacting the incubated pre-treatment reaction mixture with immobilized JCV VLP under conditions suitable for antibodies against other polyoma viruses that cross-react with JCV VLP to bind the immobilized JCV VLP, if present, and wherein the immobilized JCV VLP has been coated with a blocking agent.

23. The method of claim 22, wherein the anti-JCV antibodies in the sample, if present, are more effectively competed by the soluble JCV VLP, whereas the antibodies against other polyoma viruses that cross-react with JCV VLP, if present, preferentially detach from the complexes formed with the JCV VLP in solution and bind to the immobilized JCV VLP.

24. The method of claim 23, wherein the method comprises detecting antibodies from the sample aliquot that are bound to the immobilized JCV VLP, thereby performing a competition assay.

25. The method of claim 24, wherein the method comprises:
   (d) forming a reaction mixture comprising a second aliquot of the sample, wherein the reaction mixture comprises substantially no soluble JCV VLP;
   (e) contacting the reaction mixture of (d) to a substrate comprising immobilized JCV under conditions suitable for anti-JCV antibodies in the second aliquot to bind the immobilized JCV, if present; and
   (f) detecting antibodies from the second aliquot that are bound to the immobilized JCV VLP, if present, thereby performing a primary assay.

26. The method of claim 25, wherein the method further comprises:
   (g) comparing a detected level of antibodies that are bound to the immobilized JCV VLP in the competition assay to a detected level of antibodies that are bound to the immobilized JCV VLP in the primary assay, such that a decrease in the detected level in the competition assay compared to the primary assay indicates the sample is positive for anti-JCV antibody, and a change in the detected level below a specified percentage indicates that there is no JCV-specific antibody present in the sample.

* * * * *